(12) United States Patent
Lollo et al.

(10) Patent No.: US 7,759,319 B2
(45) Date of Patent: Jul. 20, 2010

(54) OLIGOMERIC COMPOUNDS AND COMPOSITIONS FOR USE IN MODULATION OF PRI-MIRNAS

(75) Inventors: Bridget Lollo, Encinitas, CA (US); Ravi Jain, Carlsbad, CA (US)

(73) Assignee: Regulus Therapeutics Inc., Carlsbad, CA (US)

( * ) Notice: Subject to any disclaimer, the term of this patent is extended or adjusted under 35 U.S.C. 154(b) by 351 days.

(21) Appl. No.: 11/329,992

(22) Filed: Jan. 10, 2006

(65) Prior Publication Data

US 2006/0252722 A1 Nov. 9, 2006

Related U.S. Application Data

(63) Continuation-in-part of application No. 10/909,125, filed on Jul. 30, 2004.

(60) Provisional application No. 60/492,056, filed on Jul. 31, 2003, provisional application No. 60/516,303, filed on Oct. 31, 2003, provisional application No. 60/531,596, filed on Dec. 19, 2003, provisional application No. 60/562,417, filed on Apr. 14, 2004, provisional application No. 60/642,807, filed on Jan. 10, 2005.

(51) Int. Cl.
*A61K 31/70* (2006.01)
*C07H 21/04* (2006.01)

(52) U.S. Cl. .................. 514/44; 536/23.1; 536/24.5

(58) Field of Classification Search .................. None
See application file for complete search history.

(56) References Cited

U.S. PATENT DOCUMENTS

| 5,801,154 A | 9/1998 | Baracchini et al. |
|---|---|---|
| 6,258,601 B1 * | 7/2001 | Monia et al. ................. 435/375 |
| 2003/0228691 A1 | 12/2003 | Lewis et al. |
| 2004/0053411 A1 | 3/2004 | Cullen et al. |
| 2004/0053876 A1 | 3/2004 | Turner et al. |
| 2004/0058886 A1 | 3/2004 | Scaringe |
| 2004/0086884 A1 | 5/2004 | Beach et al. |
| 2004/0086911 A1 | 5/2004 | Cabello et al. |
| 2006/0247193 A1 | 11/2006 | Taira et al. |
| 2006/0252722 A1 | 11/2006 | Lollo et al. |
| 2007/0049547 A1 | 3/2007 | Esau et al. |

FOREIGN PATENT DOCUMENTS

| WO | 8809810 A1 | 12/1988 |
|---|---|---|
| WO | WO 03/020931 | 3/2003 |
| WO | WO 03/029459 | 4/2003 |
| WO | WO 03/093441 | 11/2003 |
| WO | WO 2004/044123 | 5/2004 |
| WO | WO 2004/057017 | 7/2004 |

OTHER PUBLICATIONS

Boutla et al. Nucleic Acids Research 2003, vol. 31, pp. 4973-4980.*
Calin et al. PNAS 2002, vol. 99, pp. 15524-15529.*
Baker, B. et al., "2'-O-(2-Methoxy)ethyl-modified Anti-intercellular Adhesion Molecule 1 (ICAM-1) Oligonucleotides Selectively Increased the ICAM-1 mRNA Level and Inhibit Formation of the ICAM-1 Translation Initiation Complex in Human Umbilical Vein Endothelial Cells," J. Biol. Chem. (1997) 272(18):11994-12000.
Karras, J. G. et al., "Deletion of Individual Exons and Induction of Soluble Murine Interleukin-5 Receptor-Alpha Chain Expression through Antisense Oligonucleotide-Mediated Redirection of Pre-mRNA Splicing," Mol. Pharmacol. (2000) 58(2):380-387.
Mercatante, D. R. et al., "Modification of Alternative Splicing by Antisense Oligonucleotides as a Potential Chemotherapy for Cancer and Other Diseases," Curr. Cancer Drug Targets (2001) 1(3):211-230.
Monia, B. P. et al., "Evaluation of 2'-Modified Oligonucleotides Containing 2'-Deoxy Gaps as Antisense Inhibitors of Gene Expression," J. Biol. Chem. (1993) 268(19):14514-14522.
Kawasaki, H. et al., "Functional analysis of microRNAs during the retinoic acid-induced neuronal differentiation of human NT2 cells," *Nucleic Acids Res Suppl.* (2003) (3):243-4.
Brennecke, J. et al., "Towards a complete description of the microRNA complement of animal genomes," *Genome Biol,* (2003) 4(9):228.
Carrington, J. C. et al, "Role of MicroRNAs in Plant and Animal Development." *Science* (2003) 301(5631):336-338.
Smalheiser, N. R., "EST analyses predict the existence of a population of chimeric microRNA precursor-mRNA transcripts expressed in normal human and mouse tissues," *Genome Biol.* (2003) 4(7):403.
Baehrecke, E. H., "miRNAs: Micro Managers of Programmed Cell Death," *Curr. Biol.* (2003) 13:R473-R475.
Ambros, V., "MicroRNA Pathways in Flies and Worms: Growth, Death, Fat, Stress, and Timing," *Cell* (2003) 113:673-6. Erratum in: *Cell* (2003) 114:269.
Kawasaki, H. et al., "Hes1 is a target of microRNA-23 during retinoic-acid-induced neuronal differentiation of NT2 cells," *Nature* (2003) 423(6942):838-842.
Seitz, H. et al., "Imprinted microRNA genes transcribed antisense to a reciprocally imprinted retrotransposon-like gene," *Nat Genet.* (2003) 34(3):261-262.

(Continued)

*Primary Examiner*—Tracy Vivlemore
(74) *Attorney, Agent, or Firm*—Pepper Hamilton LLP

(57) ABSTRACT

Compounds, compositions and methods are provided for modulating the levels expression, processing and function of pri-miRNAs. In particular, methods and compounds are provided for the modulation of the levels, expression, processing or function of polycistronic pri-miRNAs. The compositions comprise oligomeric compounds targeted to small non-coding RNAs and pri-miRNAs. Further provided are methods for selectively modulating pri-miRNA levels in a cell. Also provided are methods for identifying oligomeric compounds that result in increase pri-miRNA levels when contacted with a cell.

20 Claims, No Drawings

OTHER PUBLICATIONS

Xu, P. et al, "The *Drosophila* MicroRNA Mir-14 Suppresses Cell Death and Is Required for Normal Fat Metabolism," *Curr Biol.* (2003) 13(9):790-795.

Lim, L. P. et al., "Vertebrate MicroRNA Genes," *Science* (2003) 299(5612):1540.

Doench, J. et al., "siRNAs can function as miRNAs," *Genes Dev.* (2003) 17(4):438-442.

Zeng, Y. et al., "Sequence requirements for micro RNA processing and function in human cells," *RNA* (2003) 9(1):112-123.

Dostie, J. et al., "Numerous microRNPs in neuronal cells containing novel microRNAs," *RNA* (2003) 9(2):180-186.

Lagos-Quintana, M. et al., "New microRNAs from mouse and human," *RNA* (2003) 9(2):175-179.

Calin, G. A. et al., "Frequent deletions and down-regulation of micro-RNA genes *miR15* and *miR16* at 13q14 in chronic lymphocytic leukemia," *PNAS* (2002) 99(24):15524-15529.

Moss, E. G. et al., "MicroRNAs: Something New Under the Sun," *Curr. Biol.* (2002) 12(20):R688-R690.

Caudy, A. A. et al., "Fragile X-related protein and VIG associate with the RNA interference machinery," *Genes Dev.* (2002) 16(19):2491-2496.

Lee, Y. et al., "MicroRNA maturation: stepwise processing and subcellular localization." *EMBO J.* (2002) 21(17):4663-4670.

Hutvagner, G. et al., "A microRNA in a Multiple-Turnover RNAi Enzyme Complex," *Science* (2002) 297(5589):2056-2060.

Pasquinelli, A. E. et al., "Control of Developmental Timing by MicroRNAs and Their Targets," *Annu. Rev. Cell Dev. Biol.* (2002) 18:495-513.

McManus, M. T. et al., "Gene silencing using micro-RNA designed hairpins," *RNA* (2002) 8(6):842-850.

Zeng, Y. et al., "Both Natural and Designed Micro RNAs Can Inhibit the Expression of Cognate mRNAs When Expressed in Human Cells," *Mol. Cell.* (2002) 9(6):1327-1333.

Lagos-Quintana, M. et al., "Identification of Tissue-Specific MicroRNAs from Mouse," *Curr. Biol,* (2002) 12(9):735-739.

Pasquinelli, A. E., "MicroRNAs: deviants no longer," *Trends Genet.* (2002) 18(4):171-173.

Mourelatos, Z. et al., "miRNPs: a novel class of ribonucleoproteins containing numerous microRNAs," *Genes Dev.* (2002) 16(6):720-728.

Lai, E. C., "Micro RNAs are complementary to 3' UTR sequence motifs that mediate negative post-transcriptional regulation," *Nat Genet.* (2002) 30(4):363-364.

Ambros, V., "microRNAs: Tiny Regulators with Great Potential," *Cell* (2001) 107(7):823-826.

Novina, C. D. et al., "The RNAi revolution," *Nature* (2004) 430(6996):161-164.

Bonnet, E. et al., "Evidence that microRNA precursors, unlike other non-coding RNAs, have lower folding free energies than random sequences," *Bioinformatics* (2004) 20(17):2911-2917.

He, L. et al., "MicroRNAs: Small RNAs With a Big Role in Gene Regulation," *Nat. Rev. Genet.* (2004) 5(7):522-531.

Scherr, M. et al., "RNAi in functional genomics," *Curr. Opin. Mol. Ther,* (2004) 6(2):129-135.

Suh, M. R. et al., "Human embryonic stem cells express a unique set of microRNAs," *Dev. Biol.* (2004) 270(2):488-498.

Takamizawa, J. et al., "Reduced Expression of the *let-7* MicroRNAs in Human Lung Cancers in Association with Shortened Postoperative Survival," *Cancer Res.* (2004) 64(11):3753-3756.

Murchison, E. P. et al., "miRNAs on the move: miRNA biogenesis and the RNAi machinery," *Curr. Opin. Cell Biol.* (2004) 16(3):223-229.

Bartel, D. P. et al., "Micromanagers of gene expression: the potentially widespread influence of metazoan microRNAs," *Nat. Rev. Genet.* (2004) 5(5):396-400.

Kim, V, N., "MicroRNA precursors in motion: exportin-5 mediates their nuclear export," *Trends Cell Biol.* (2004) 14(4):156-159.

Kiriakidou, M. et al., "A combined computational-experimental approach predicts human microRNA targets," *Genes Dev.* (2004) 18(10):1165-1178.

Chapman, E. J. et al., "Viral RNA silencing suppressors inhibit the microRNA pathway at an intermediate step," *Genes Dev.* (2004) 18(10):1179-1186.

Pfeffer, S. et al., "Identification of Virus-Encoded MicroRNAs," *Science* (2004) 304(5671):734-736.

Yekta, S. et al., "MicroRNA-Directed Cleavage of *HOXB8* mRNA," *Science* (2004) 304(5670):594-596.

Ambros, V. et al., "Identification of microRNAs and Other Tiny Noncoding RNAs by cDNA Cloning," *Methods Mol. Biol.* (2004) 265:131-158.

Lee, Y. S. et al., "Distinct Roles for *Drosophila* Dicer-1 and Dicer-2 in the siRNA/miRNA Silencing Pathways," *Cell* (2004) 117(1):69-81.

Tijsterman, M. et al., "Dicers at RISC: The Mechanism of RNAi," *Cell* (2004) 117(1):1-3.

Kawasaki, H. et al., "World of small RNAs: from ribozymes to siRNA and miRNA," *Differentiation* (2004) 72(2-3):58-64.

Ruvkun, G. et al., "The 20 Years It Took to Recognize the Importance of Tiny RNAs," *Cell* (2004) S116:S93-S96.

Lee, R. et al., "A Short history of a Short RNA," *Cell* (2004) S116:S89-S92.

Hutvagner, G. et al., "Sequence-Specific Inhibition of Small RNA Function," *PLoS Biol.* (2004) 2(4):0001-0011.

Matzke, M. et al., "Genetic analysis of RNA-mediated transcriptional gene silencing," *Biochim. Biophys. Acta.* (2004) 1677(1-3):129-141.

Rajewsky, N. et al., "Computational identification of microRNA targets," *Dev. Biol.* (2004) 267(2):529-535.

Sempere, L. F. et al., "Expression profiling of mammalian microRNAs uncovers a subset of brain-expressed microRNAs with possible roles in murine and human neuronal differentiation," *Genome Biol.* (2004) 5(3):R13.

Siomi, H. et al., "RNA Interference: A New Mechanism by Which FMRP Acts in the Normal Brain? What Can Drosophila Teach Us?" *Ment. Retard. Dev. Disabil. Res. Rev.* (2004) 10(1):68-74.

Katayama, K. et al., "RNA interfering approach for clarifying the PPARγ pathway using lentiviral vector expressing short hairpin RNA," *FEBS Lett.* (2004) 560(1-3):178-182.

Carmell, M. A. et al., "RNase III enzymes and the initiation of gene silencing," *Nat. Struct. Mol. Biol.* (2004) 11(3):214-218.

Calin, G. A. et al., "Human microRNA genes are frequently located at fragile sites and genomic regions involved in cancers," *PNAS* (2004) 101(9):2999-3004.

Meister, G. et al., "Sequence-specific inhibition of microRNA- and siRNA-induced RNA silencing," *RNA* (2004) 10(3):544-550.

Nelson, P. T. et al., "miRNP:mRNA association in polyribosomes in a human neuronal cell line," *RNA* (2004) 10(3):387-394.

Boden, D. et al., "Enhanced gene silencing of HIV-1 specific siRNA using microRNA designed hairpins," *Nucleic Acids Res.* (2004) 32(3):1154-1158.

Huang, A. et al., "Functional silencing of hepatic microsomal glucose-6-phosphatase gene expression in vivo by adenovirus-mediated delivery of short hairpin RNA," *FEBS Lett.* (2004) 558(1-3):69-73.

Bartel, D. P., "MicroRNAs: Genomics, Biogenesis, Mechanism, and Function," *Cell* (2004) 116(2):281-297.

Bohnsack, M. T. et al., "Exportin 5 is a RanGTP-dependent dsRNA-binding protein that mediates nuclear export of pre-miRNAs," *RNA* (2004) 10(2):185-191.

Lai, E. C. et al., "Complementary miRNA pairs suggest a regulatory role for miRNA:miRNA duplexes," *RNA* (2004) 10(2):171-175.

Jin, P. et al., "Biochemical and genetic interaction between the fragile X mental retardation protein and the microRNA pathway," *Nat. Neurosci.* (2004) 7(2):113-117.

Lewis, B. P. et al., "Prediction of Mammalian MicroRNA Targets," *Cell* (2003) 115(7):787-798.

Metzler, M. et al., "High Expression of Precursor MicroRNA-155/ BIC RNA in Children with Burkitt Lymphoma," *Genes Chromosomes Cancer* (2004) 39(2):167-169.

Kim, J. et al., "Identification of many microRNAs that copurify with polyribosomes in mammalian neurons," *PNAS* (2004) 101(1):360-365.

Griffiths-Jones, S. "The microRNA Registry," *Nucleic Acids Res.* (2004) 32 Database issue:D109-111.

Chen, C. Z. et al., "MicroRNAs Modulate Hematopoietic Lineage Differentiation," *Science* (2004) 303(5654):83-86.

Lund, E. et al., "Nuclear Export of MicroRNA Precursors," *Science* (2004) 303(5654):95-98. Epub Nov. 20, 2003.

Basyuk, E. et al., "Human let-7 stem-loop precursors harbor features of RNase III cleavage products," *Nucleic Acids Res.* (2003) 31(22):6593-6597.

Michael, M. Z. et al., "Reduced Accumulation of Specific MicroRNAs in Colorectal Neoplasia," *Mol. Cancer Res.* (2003) 1(12):882-891.

Khvorova, A. et al., "Functional siRNAs and miRNAs Exhibit Strand Bias," *Cell* (2003) 115(2):209-216.

McManus, M. T., "MicroRNAs and cancer," *Semin. Cancer Biol.* (2003) 13(4):253-258.

Lee, Y. et al., "The nuclear RNase III Drosha initiates microRNA processing," *Nature* (2003) 425(6956):415-419.

Bergmann, A. et al., "HIDden targets of microRNAs for growth control," *Trends Biochem. Sci.* (2003) 28(9):461-463.

Ke, X. S. et al., "MicroRNAs: key participants in gene regulatory networks," *Curr. Opin. Chem. Biol.* (2003) 7(4):516-523.

Boutla, A. et al., "Developmental defects by antisense-mediated inactivation of microRNAs 2 and 13 in *Drosophila* and the identification of putative target genes," *Nucleic Acids Res.* (2003) 31(17):4973-4980.

Houbaviy, H. B. et al., "Embryonic Stem Cell-Specific MicroRNAs," *Dev. Cell.* (2003) 5(2):351-358.

Schramke, V. et al., "Hairpin RNAs and Retrotransposon LTRs Effect RNAi and Chromatin-Based Gene Silencing," *Science* (2003) 301(5636):1069-1074.

Zeng, Y. et al., "MicroRNAs and small interfering RNAs can inhibit mRNA expression by similar Mechanisms," *PNAS* (2003) 100(17):9779-9784.

Final Rejection Office Action for U.S. Appl. No. 10/909,125 dated Mar. 16, 2007.

International Search Report for WO 2005/013901 dated Dec. 13, 2005.

Office Action for U.S. Appl. No. 10/909,125 dated Jun. 22, 2006.

Office Action for U.S. Appl. No. 10/909,125 dated Nov. 13, 2007.

Written Opinion for WO 2005/013901 dated Dec. 13, 2005.

* cited by examiner

US 7,759,319 B2

OLIGOMERIC COMPOUNDS AND COMPOSITIONS FOR USE IN MODULATION OF PRI-MIRNAS

CROSS-REFERENCE TO RELATED APPLICATIONS

This application is a continuation-in-part of U.S. application Ser. No. 10/909,125, filed Jul. 30, 2004, which claims priority under 35§ U.S.C. 119(e) to U.S. provisional applications Ser. No. 60/492,056 filed Jul. 31, 2003, Ser. No. 60/516,303 filed Oct. 31, 2003, Ser. No. 60/531,596 filed Dec. 19, 2003, and Ser. No. 60/562,417 filed Apr. 14, 2004, each which is incorporated herein by reference in its entirety. The present application also claims priority under 35§U.S.C. 119(e) to U.S. Provisional Application No.: 60/642,807 filed on Jan. 10, 2005, which is hereby incorporated by reference in its entirety.

SEQUENCE LISTING

A paper copy of the sequence listing and a computer-readable form of the sequence listing, on diskette, containing the file named CORE0016USP1SEQ.txt, which was created on Jan. 10, 2006, are herein incorporated by reference.

FIELD OF THE INVENTION

The present invention provides compositions and methods for modulation of small non-coding RNAs, particularly pri-miRNAs. In particular, this invention relates to compounds, particularly oligomeric compounds, which, in some embodiments, hybridize with or sterically interfere with nucleic acid molecules comprising or encoding small non-coding RNA targets, including pri-miRNAs.

BACKGROUND OF THE INVENTION

MicroRNAs (miRNAs) are small (approximately 21-22 nucleotides in length, these are also known as "mature" miRNA), non-coding RNA molecules encoded in the genomes of plants and animals. These highly conserved, endogenously expressed RNAs regulate the expression of genes by binding to the 3'-untranslated regions (3'-UTR) of specific mRNAs. MiRNAs may act as key regulators of cellular processes such as cell proliferation, cell death (apoptosis), metabolism, and cell differentiation. On a larger scale, miRNA expression has been implicated in early development, brain development, disease progression (such as cancers and viral infections). There is speculation that in higher eukaryotes, the role of miRNAs in regulating gene expression could be as important as that of transcription factors. More than 200 different miRNAs have been identified in plants and animals (Ambros et al., Curr. Biol., 2003, 13, 807-818). Mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

The current model of miRNA processing involves primary miRNA transcripts being processed by a nuclear enzyme in the RNase III family known as Drosha, into approximately 70 nucleotide-long pre-miRNAs (also known as stem-loop structures, hairpins, pre-mirs or foldback miRNA precursors) which are subsequently processed by the Dicer RNase into mature miRNAs, approximately 21-25 nucleotides in length. It is believed that, in processing pri-miRNA into the pre-miRNA, the Drosha enzyme cuts pri-miRNA at the base of the mature miRNA, leaving a 2-nt 3' overhang (Ambros et al., RNA, 2003, 9, 277-279; Bartel and Bartel, Plant Physiol., 2003, 132, 709-717; Shi, Trends Genet., 2003, 19, 9-12; Lee, et al., EMBO J., 2002, 21(17), 4663-4670; Lee, et al., Nature, 2003, 425, 415-419). The 3' two-nucleotide overhang structure, a signature of RNaseIII cleavage, has been identified as a critical specificity determinant in targeting and maintaining small RNAs in the RNA interference pathway (Murchison, et al., Curr. Opin. Cell. Biol., 2004, 16, 223-9). Both the primary RNA transcripts (pri-miRNAs) and foldback miRNA precursors (pre-miRNAs) are believed to be single-stranded RNA molecules with at least partial double-stranded character, often containing smaller, local internal hairpin structures. In some instances, primary miRNA transcripts are processed such that one single-stranded mature miRNA molecule is generated from one arm of the hairpin-like structure of pri-miRNA; such primary miRNA transcripts are often referred to as monocistronic pri-miRNA transcripts. Alternatively, a pri-miRNA transcript contains multiple hairpin structures, and different hairpins give rise to different miRNAs. These are considered polycistronic miRNA transcripts, and each hairpin containing a mature miRNA is given a unique gene name and the miRNA present on a single transcript may be refered to as a "cluster" of such miRNAs. Examples of polycistronic miRNA clusters include the miR-17-92 cluster and the miR-15/miR-16-1 cluster.

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662).

Links between miRNAs, including miRNA families and clusters, and human disease have been also been identified. Many miRNAs are de-regulated in primary human tumors (Calin et al., Proc. Natl. Acad. Sci, 2002, 99, 15524-15529; Calin et al., Proc. Natl. Acad. Sci, 2004, 101, 11755-11760; He et al., Nature, 2005, 435, 828-833; Lu et al., Nature, 2005, 435, 834). Moreover, many human miRNAs are located at genomic regions linked to cancer (Calin et al., Proc. Natl. Acad. Sci, 2004, 101, 2999-3004; McManus, 2003, Semin. Cancer Biol, 13, 252-258; He et al., Nature, 2005, 435, 828-833). Mir-15a and mir-16-1, which are derived from a polycistronic miRNA, are located within a 30-kb region chromosome 13q14, a region deleted in more than half of B cell chronic lymphocytic leukemias (B-CLL). Both mir-15a and mir-16-1 are deleted or down-regulated in the majority of CLL cases (Calin et al., Proc. Nat. Acad. Sci, 2002, 99, 15524-15529).

Families of miRNAs are characterized by nucleotide identity at positions 2-8 of the miRNA, a region known as the seed sequence. Lewis et al. describe several miRNA families, as well as miRNA superfamilies, which are characterized by related seed sequences (Lewis et al. 2005).

MiRNAs are thought to exercise post-transcriptional control in most eukaryotic organisms and have been detected in plants and animals as well as certain viruses. A large number of miRNAs have been identified from several species (see for example PCT Publication WO 03/029459 and Published US Patent Applications 20050222399, 20050227934, 20050059005 and 20050221293) and many more have been bioinformatically predicted. Many of these miRNA are conserved across species, but species specific miRNA have also been identified (Pillai, RNA, 2005, 11, 1753-1761).

Small non-coding RNA-mediated regulation of gene expression is an attractive approach to the treatment of diseases as well as infection by pathogens such as bacteria, viruses and prions and other disorders associated with RNA expression or processing. By way of example, modulating the expression or processing of miR-122 may present an approach for antiviral therapies, studies of a genetic interaction between miR-122 and the 5' noncoding region of the hepatitis C viral genome suggest that miR-122 is likely to facilitate replication of the hepatitis C viral RNA (Jopling, et al., *Science,* 2005, 5740, 1577-1581).

Consequently, there is a need for agents that regulate gene expression via the mechanisms mediated by small non-coding RNAs. Identification of oligomeric compounds that can increase or decrease gene expression or activity by modulating the levels of miRNA in a cell is therefore desirable.

The present invention therefore provides oligomeric compounds and methods useful for modulating the levels, expression, or processing of pri-miRNAs, including those relying on mechanisms of action such as RNA interference and dsRNA enzymes, as well as antisense and non-antisense mechanisms. One having skill in the art, once armed with this disclosure will be able, without undue experimentation, to identify compounds, compositions and methods for these uses.

SUMMARY OF THE INVENTION

The present invention provides oligomeric compounds, especially nucleic acid and nucleic acid-like oligomeric compounds, which are targeted to, or mimic, nucleic acids comprising or encoding small non-coding RNAs, and which act to modulate the levels of small non-coding RNAs, particularly pri-miRNAs, or interfere with their function.

The present invention also provides oligomeric compounds, especially nucleic acid and nucleic acid-like oligomeric compounds, which are targeted to pri-miRNAs, and which act to modulate the levels of pri-miRNAs, or interfere with their processing or function. The present invention further provides oligomeric compounds that target a region flanking or overlapping a Drosha recognition region within a pri-miRNA. Additionally, the present invention provides oligomeric compounds that target a region flanking or overlapping a Drosha cleavage site. The present invention also provides oligomeric compounds that increase levels of a pri-miRNA. For example, the present invention provides oligomeric compounds 15 to 30 nucleobases in length targeted to a Drosha recognition region within a polycistronic pri-miRNA transcript. The polycistronic pri-miRNA transcript can be that from which miR-15a and miR-16-1 are derived. The Drosha recognition region can be that of miR-16-1. Such oligomeric compounds may be antisense oligonucleotides, and may contain one or more chemical modifications. Additionally, such oligomeric compounds are capable of increasing pri-miR-15a and pri-miR-16-1 levels.

Also provided are methods of modulating the levels of small non-coding RNAs, particularly pri-miRNAs, in cells, tissues or animals comprising contacting said cells, tissues or animals with one or more of the compounds or compositions of the invention.

Further provided are methods of modulating the levels of miRs derived from a polycistronic pri-miR transcript in a cell comprising selecting a polycistronic pri-miR transcript, selecting a Drosha recognition region of a single miRNA derived from the selected polycistronic pri-miR transcript, selecting an oligomeric compound 15 to 30 nucleotides in length targeted to or sufficiently complementary to the selected Drosha recognition region, and contacting the cell with the oligomeric compound. Such methods include modulating the levels of a single mature miRNA derived from the selected polycistronic pri-miRNA, or alternatively modulating the levels of two or more mature miRNAs derived from the selected polycistronic pri-miRNA. Also provided are methods of modulating the levels of pri-miRNA-15a and pri-miR-16-1 comprising contacting a cell with an oligomeric compound targeted to or sufficiently complementary to Drosha-recognition regions on pri-miRNA-16-1 or pri-miRNA-15a.

The present invention provides methods for selectively modulating a single member of a miR family in a cell comprising selecting a member of a miR family derived from a pri-miR transcript, identifying one or more oligomeric compounds targeted to or sufficiently complementary to the Drosha recognition region of a the selected pri-miR transcript, wherein the identified oligomeric compounds lack sufficient complementarity to the Drosha recognition regions of pri-miR transcripts from which other members of the miR family are derived, and contacting the cell with such an identified oligomeric compound.

The present invention also provides oligomeric compounds comprising a first strand and a second strand wherein at least one strand contains a modification and wherein a portion of one of the oligomeric compound strands is capable of hybridizing to a small non-coding RNA target nucleic acid.

The present invention also provides oligomeric compounds comprising a first region and a second region and optionally a third region wherein at least one region contains a modification and wherein a portion of the oligomeric compound is capable of hybridizing to a small non-coding RNA target nucleic acid.

The present invention provides methods for identifying oligomeric compounds capable of modulating pri-miRNA levels. A pri-miRNA is selected, and oligomeric compounds are designed such that they are targeted to or sufficiently complementary to various target segments within a pri-miRNA sequence, including oligomeric compounds targeted to and overlapping the mature miRNA sequence within the pri-miRNA. An increase in the level of a pri-miRNA in cells contacted with the oligomeric compounds as compared to cells not contacted with the oligomeric compounds indicates that the oligomeric compound modulates the pri-miRNA level.

The present invention further provides methods for identifying small molecules capable of modulating pri-miRNA levels. A pri-miRNA is selected, and small molecules are evaluated for their ability of modulate pri-miRNA levels. The small molecules may bind to the regions of the pri-miR containing or overlapping the mature miRNA sequence, or the Drosha recognition region. An increase in the level of a pri-miRNA in cells contacted with the small molecules as compared to cells not contacted with the small molecules indicates that the small molecule modulates the pri-miRNA levels.

DETAILED DESCRIPTION

The present invention provides methods for modulating the levels, expression, processing or function of small non-coding RNAs, particularly pri-miRNAs. Such methods are useful for the modulation of a single mature miRNA derived from a polycistronic pri-miRNA transcript. Alternatively, such methods are useful for the modulation of multiple mature miRNAs derived from a polycistronic pri-miRNA transcript.

A polycistronic pri-miRNA transcript ifs selected for modulation in a cell, and a Drosha recognition region on the selected polycistronic pri-miRNA is identified. The Drosha recognition region is that of a single miRNA derived from the polycistronic pri-miRNA transcript. One or more oligomeric compounds are identified that are targeted to or sufficiently complementary to the identified Drosha recognition region, and a cell is contacted with the oligomeric compound. The contacting of the cell with an oligomeric compound targeted to or sufficiently complementary to the identified Drosha recognition region results in a modulation of the level of a pri-miRNA, as evidenced by a change in the level of the pri-miRNA as compared to the level in cells not contacted with the oligomeric compound. An increase or decrease in the pri-miRNA level indicates that the oligomeric compound modulates the level, expression, or processing of the pri-miRNA.

As used herein, the term "polycistronic pri-miRNA transcript" or "polycistronic miRNA transcript" refers to a pri-miRNA transcript containing multiple hairpin structures, each of which gives rise to a different miRNA; each hairpin is given a unique gene name. In one aspect, miRNAs derived from a polycistronic miRNA transcript may be spatially or temporally coordinately expressed, i.e. they have similar expression profiles in a particular cell or tissue or in a particular stage of cell growth or organism development, respectively. In an alternative aspect, miRNAs derived from a polycistronic pri-miRNA are not expressed in a coordinated manner. Examples of polycistronic miRNA clusters include, but are not limited to, the miR-17-92 cluster and the miR-15/miR-16-1 cluster.

As used herein, the term "miRNA cluster" refers to two or more miRNAs whose transcription and/or processing is controlled in a coordinated manner. The coordinated expression and/or processing of an miRNA cluster may be controlled spatially or temporally, i.e. controlled within a particular tissue or cell type or during a particular stage of cell growth or organism development, respectively. Examples of miRNA clusters are known in the art and include, but are not limited to, miR-23/27/24-2 containing three miRNAs; miR-17/18/19a/20/19b-1 containing five miRNAs; and miR-17-92 containing seven miRNAs. Additionally, miR-15a and miR-16-1 comprise a miRNA cluster.

As used herein, the term "miRNA family" refers to a plurality of miRNAs that are related by nucleotide sequence. Thus, the members of an miRNA family are also known as "related miRNAs". Each member of a miRNA family shares an identical seed sequence. As used herein, the term "seed sequence" refers to nucleotides 2 to 6 or 2 to 7 from the 5'-end of a mature miRNA sequence. Examples of miRNA families are known in the art and include, but are not limited to, the let-7 family (having 9 miRNAs), the miR-15 family (comprising miR-15a, miR-15b, miR-16-1, and miR-195), and the miR-181 family (comprising miR-181a, miR-181b, and miR-181c).

Polycistronic miRNA transcript, miRNA clusters and miRNA families have been found to be aberrantly expressed in disease states, i.e. miRNAs derived from the a polycistronic miRNA transcript, or miRNAs that are members of miRNA families or clusters are collectively present at higher or lower levels in a diseased cell or tissue as compared to healthy cell or tissue. In one embodiment, a polycistronic miRNA transcript, a miRNA cluster, or an miRNA family that is aberrantly expressed in a disease state is selected for modulation using the oligomeric compounds and methods of the present invention.

As used herein, the term "monocistronic pri-miRNA transcript" or "monocistronic miRNA transcript" refers to a pri-miRNA from which a single pre-miRNA, and consequently a single miRNA, is derived. Examples of monocistronic pri-miRNA transcripts include, but are not limited to, those transcripts containing miR-122, miR-21, miR-1, and miR-30a.

As used herein, the term "miRNA precursor" is used to encompass, without limitation, primary RNA transcripts, pri-miRNAs, including polycistronic pri-miRNAs and monocistronic pri-miRNAs, and pre-miRNAs.

As used herein, the term "Drosha recognition region" within a pri-miRNA transcript encompasses the mature miRNA as well as up to 25 nucleotides in the 5' direction relative to the 5' Drosha cleavage site of such mature miRNA, and up to 50 nucleotides in the 3' direction relative to the 3' Drosha cleavage site of such mature miRNA. In additional embodiments, the Drosha recognition region encompasses the mature miRNA and up to 15 nucleotides in the 5' direction relative to the 5' Drosha cleavage site of such mature miRNA, and up to 40 nucleotides in the 3' direction relative to the 3' Drosha cleavage site of such mature miRNA. In some aspects, the Drosha recognition region is a region strongly affected by oligomeric compounds targeted to this region, i.e. the targeting of oligomeric compounds to this region of a pri-miRNA results in a greater than 3.5-fold increase in the level of the pri-miRNA. In other aspects, the level of the pri-miRNA is moderately affected by oligomeric compounds targeted to this region, i.e. the targeting of oligomeric compounds to this Drosha recognition region results in a 1.5 to 2.5-fold increase in the levels of the pri-miRNA. In further aspects, the targeting of a pri-miRNA with an oligomeric compound of the invention affects the processing of one or more miRNAs on a polycistronic pri-miRNA.

As used herein, the term "Drosha cleavage site" is used to refer to a site approximately 22 nucleobases from the junction of the terminal hairpin loop and the stem of a pri-miRNA. One end of the miRNA is determined by selection of the cleavage site by the Drosha enzyme.

In one embodiment, a polycistronic pri-miRNA transcript containing a preferentially processed miRNA is selected for modulation. miRNAs within a cluster or derived from a polycistronic pri-miRNA transcript may exhibit different levels or patterns of expression. For example, a first miRNA derived from a polycistronic miRNA transcript may be a "preferentially processed miRNA", i.e. an miRNA that is found in a cell at higher levels, than a second miRNA derived from the same polycistronic miRNA transcript. Targeting a preferentially processed miRNA or the Drosha recognition region of a preferentially processed miRNA may result in accumulation of the entire pri-miRNA transcript, which in turn results in the reduction of the levels of multiple miRNAs derived from the polycistronic pri-miRNA transcript. In one non-limiting example, within the miR-15 family, miR-16-1 is found at higher levels than miR-15a. Oligomeric compounds targeted to the pri-miR-16-1 Drosha recognition region result in increased pri-miR-15a and pri-miR-16-1 levels, whereas oligomeric compounds targeted to or sufficiently complementary to the pri-miR-15a Drosha recognition region result in the increase of pri-miR-15a. Preferentially processed miRNA may differ among cell types, tissues, or developmental stages.

The present invention provides methods for the selective modulation of a single member of a miRNA family in a cell. The presence of identical seed sequences amongst miRNA family members may preclude the identification of oligomeric compounds which are sufficiently complmentary to hybridize to only a single member of the miRNA family. Thus, in the methods provided herein, an oligomeric compound is selected to that is sufficiently complementary to the Drosha recognition region of the selected miRNA, resulting in the reduction of pri-miRNA levels or inhibition of pri-miRNA processing, which in turn results in the reduction of the levels of the selected miRNA. A member of a miRNA family, derived from a polycistronic or monocistronic pri-miRNA transcript, is selected for modulation. And oligomeric compound is identified which is targeted to or sufficiently complementary to the Drosha recognition region of the selected miRNA and which also lacks sufficient complementarity to the Drosha recognition regions of one or more of the remaining members of the miRNA family. Contacting a cell with the identified oligomeric compound results in the modulation of the single selected member of the miRNA family, while the remaining miRNA family members are not modulated.

The present invention provides methods of identifying a Drosha recognition region in a pri-miRNA. Oligomeric compounds are designed such that they are targeted to or sufficiently complementary to various target segments within a pri-miRNA sequence, including oligomeric compounds targeted or overlapping the mature miRNA sequence within the pri-miRNA. An increase in the level of a pri-miRNA in cells contacted with the oligomeric compounds as compared to cells not contacted with the oligomeric compounds indicates that the oligomeric compound modulates pri-miRNA levels. As exemplified herein, the pri-miR-16-1 Drosha recognition region encompasses: the mature miR-16-1 sequence; up to 25 nucleotides in the 5' direction relative to the 5' Drosha cleavage site within pri-miR-16-1; and up to 50 nucleotides in the 3' direction relative to the 3' Drosha cleavage site within pri-miR-16-1. For purposes of distinguising the portion of a polycistronic pri-miRNA transcript surrounding a given mature miRNA sequence, the pri-miRNA is herein referred as pri-miR-X, wherein "X" is the name of the mature miRNA. For example, pri-miR-16-1 is the region of the polycistronic pri-miRNA transcript containing mature miR16-1. Alternatively, the pri-miRNA is referred to as "miR-X pri-miRNA".

Once the Drosha recognition region in a pri-miRNA has been identified, one of skill in the art could identify small molecules capable of binding to the Drosha recognition region of a pri-miRNA. Methods for identifying such small molecules are well known in the art, and involve the use of mass spectrometry to identify small molecule compounds capable of binding to structured RNA (e.g. U.S. Pat. Nos. 6,787,315; 6,770,486; 6,730,485; 6,656,690, each of which is herein incorporated by reference in its entirety).

The present invention also provides oligomeric compounds useful in, for example, the modulation of expression, endogenous levels, processing or function of small non-coding RNAs, in particular, pri-miRNAs.

As used herein, the term "small non-coding RNA" is used to encompass, without limitation, a polynucleotide molecule ranging from about 17 to about 450 nucleotides in length, which can be endogenously transcribed or produced exogenously (chemically or synthetically), but is not translated into a protein. Examples of small non-coding RNAs include, but are not limited to, primary miRNA transcripts (also known as pri-pre-miRNAs, pri-mirs, pri-miRs and pri-miR-NAs, which range from around 70 nucleotides to about 450 nucleotides in length and often taking the form of a hairpin structure); pre-miRNAs (also known as pre-mirs, pre-miRs and foldback miRNA precursors, which range from around 50 nucleotides to around 110 nucleotides in length); miRNAs (also known as microRNAs, Mirs, miRs, mirs, and mature miRNAs, and generally refer either to double-stranded intermediate molecules around 17 to about 25 nucleotides in length, or to single-stranded miRNAs, which may comprise a bulged structure upon hybridization with a partially complementary target nucleic acid molecule); or mimics of pri-miRNAs, pre-miRNAs or miRNAs. Small non-coding RNAs can be endogenously transcribed in cells, or can be synthetic oligonucleotides, in vitro transcribed polynucleotides or nucleic acid oligomeric compounds expressed from vectors. Pri-miRNAs and pre-miRNAs, or mimics thereof, may be processed into smaller molecules. Preferred small non-coding RNAs of this invention are pri-miRNAs.

Small non-coding RNAs may include isolated single-, double-, or multiple-stranded molecules, any of which may include regions of intrastrand nucleobase complementarity, said regions capable of folding and forming a molecule with fully or partially double-stranded or multiple-stranded character based on regions of perfect or imperfect complementarity.

Oligomeric compounds of the invention modulate the levels, expression or function of small non-coding RNAs, particularly those encoded within polycistronic pri-miR transcripts, by hybridizing to a nucleic acid comprising or encoding a small non-coding RNA nucleic acid target resulting in alteration of normal function by, for example, facilitating destruction of the small non-coding RNA through cleavage, by sequestration, or by sterically occluding the function of the small non-coding RNA. These oligomeric compounds may be modified to increase desired characteristics of the compounds, these modifications include, but are not limited to those which provide, improved pharmacokinetic or pharmacodynamic properties, binding affinity, stability, charge, localization or uptake.

As used herein, the terms "target nucleic acid," "target RNA," "target RNA transcript" or "nucleic acid target" are used to encompass any nucleic acid capable of being targeted including, without limitation, RNA. In a one embodiment, the nucleic acids are non-coding sequences including, but not limited to, pri-miRNAs (both polycistronic and monocistronic pri-miRNAs), pre-miRNAs, and mature miRNAs. In another embodiment, the nucleic acid targets are single- or double-stranded, or single-stranded with partial double-stranded character; may occur naturally within introns or untranslated regions of genes; and can be endogenously transcribed or exogenously produced.

In the context of the present invention, "modulation" and "modulation of expression" mean either an increase (stimulation) or a decrease (inhibition) in the amount or levels of a small non-coding RNA, nucleic acid target, an RNA or protein associated with a small non-coding RNA, or a downstream target of the small non-coding RNA (e.g., a mRNA representing a protein-coding nucleic acid that is regulated by a small non-coding RNA). Inhibition is a suitable form of modulation and small non-coding RNA is a suitable target nucleic acid. Small non-coding RNAs whose levels can be modulated include pri-miRNAs (both polycistronic and monocistronic pri-miRNAs), pre-miRNAs, and miRNAs.

In the context of the present invention, "modulation of function" means an alteration in the function of the small non-coding RNA or an alteration in the function of any cellular component with which the small non-coding RNA has an association or downstream effect.

The present invention provides, inter alia, oligomeric compounds and compositions containing the same wherein the oligomeric compound includes one or more modifications that render the compound capable of supporting modulation of the levels, expression or function of the small non-coding RNA by a degradation or cleavage mechanism.

The present invention also provides oligomeric compounds and compositions containing the same wherein the oligomeric compound includes one or more modifications that render the compound capable of blocking or interfering with the levels, expression or function of one or more small non-coding RNAs by steric occlusion.

The present invention also provides oligomeric compounds and compositions containing the same wherein the oligomeric compound includes one or more modifications or structural elements or motifs that render the compound capable of mimicking or replacing one or more small non-coding RNAs.

Oligomeric Compounds

In the context of the present invention, the term "oligomeric compound(s)" refers to polymeric structures which are capable of hybridizing to at least a region of a small non-coding RNA molecule or a target of small non-coding RNAs, or polymeric structures which are capable of mimicking small non-coding RNAs. The term "oligomeric compound" includes, but is not limited to, compounds comprising oligonucleotides, oligonucleosides, oligonucleotide analogs, oligonucleotide mimetics and combinations of these. Oligomeric compounds also include, but are not limited to, antisense oligomeric compounds, antisense oligonucleotides, siRNAs, alternate splicers, primers, probes and other compounds that hybridize to at least a portion of the target nucleic acid. Oligomeric compounds are routinely prepared linearly but can be joined or otherwise prepared to be circular and may also include branching. Separate oligomeric compounds can hybridize to form double stranded compounds that can be blunt-ended or may include overhangs on one or both termini. In general, an oligomeric compound comprises a backbone of linked monomeric subunits where each linked monomeric subunit is directly or indirectly attached to a heterocyclic base moiety. The linkages joining the monomeric subunits, the sugar moieties or sugar surrogates and the heterocyclic base moieties can be independently modified giving rise to a plurality of motifs for the resulting oligomeric compounds including hemimers, gapmers and chimeras. Modified oligomeric compounds are often preferred over native forms because of desirable properties such as, for example, enhanced cellular uptake, enhanced affinity for nucleic acid target and increased stability in the presence of nucleases. As used herein, the term "modification" includes substitution and/or any change from a starting or natural oligomeric compound, such as an oligonucleotide. Modifications to oligomeric compounds encompass substitutions or changes to internucleoside linkages, sugar moieties, or base moieties, such as those described below.

The oligomeric compounds in accordance with this invention comprise from about 8 to about 80 monomeric subunits (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 subunits in length, or any range therewithin.

In one embodiment, the oligomeric compounds of the invention are 12 to 50 monomeric subunits in length, as exemplified above.

In one embodiment, the oligomeric compounds of the invention are 13 to 80 monomeric subunits in length, as exemplified above.

In one embodiment, the oligomeric compounds of the invention are 15 to 30 monomeric subunits in length, as exemplified above.

In one embodiment, the oligomeric compounds of the invention are 17 to 25 subunits in length, as exemplified herein.

As used herein, the term "about" means ±5% of the variable thereafter.

In the context of this invention, "hybridization" means the pairing of complementary strands of oligomeric compounds. In the present invention, the mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An oligomeric compound of the invention is "specifically hybridizable" when association of the compound with the target nucleic acid interferes with the normal function of the target nucleic acid to alter the activity, disrupt the function, or modulate the level of the target nucleic acid, and there is a sufficient degree of complementarity to avoid non-specific binding of the oligomeric compound to non-target nucleic acid sequences under conditions in which specific hybridization is desired, i.e., under physiological conditions in the case of in vivo assays or therapeutic treatment, and under standard assay conditions in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated. One having ordinary skill in the art will understand variability in the experimental protocols and be able to determine when conditions are optimal for stringent hybridization with minimal non-specific hybridization events.

"Complementary," as used herein, refers to the capacity for precise pairing of two monomeric subunits regardless of where in the oligomeric compound or target nucleic acid the two are located. For example, if a monomeric subunit at a certain position of an oligomeric compound is capable of hydrogen bonding with a monomeric subunit at a certain position of a target nucleic acid, then the position of hydrogen bonding between the oligomeric compound and the target nucleic acid is considered to be a complementary position. The oligomeric compound and the target nucleic acid are "substantially complementary" to each other when a sufficient number of complementary positions in each molecule are occupied by monomeric subunits that can hydrogen bond with each other. Thus, the term "substantially complementary" is used to indicate a sufficient degree of precise pairing over a sufficient number of monomeric subunits such that stable and specific binding occurs between the oligomeric compound and a target nucleic acid. The terms "substantially complementary" and "sufficiently complementary" are herein used interchangably.

Generally, an oligomeric compound is "antisense" to a target nucleic acid when, written in the 5' to 3' direction, it comprises the reverse complement of the corresponding region of the target nucleic acid. "Antisense compounds" are also often defined in the art to comprise the further limitation of, once hybridized to a target, being able to induce or trigger a reduction in target gene expression or target nucleic acid levels.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization (e.g., a bulge, a loop structure or a hairpin structure).

In some embodiments of the invention, the oligomeric compounds comprise at least 50%, at least 60%, at least 70%, at least 75%, at least 80%, or at least 85% sequence complementarity to a target region within the target nucleic acid. In other embodiments of the invention, the oligomeric compounds comprise at least 90% sequence complementarity to a target region within the target nucleic acid. In other embodiments of the invention, the oligomeric compounds comprise at least 95% or at least 99% sequence complementarity to a target region within the target nucleic acid. For example, an oligomeric compound in which 18 of 20 nucleobases of the oligomeric compound are complementary to a target sequence would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In some embodiments of the invention, the oligomeric compounds act as mimics or replacements for small non-coding RNAs. In this case, the oligomeric compounds of the invention can comprise at least 70% sequence identity to a small non-coding RNA or a region thereof. In some embodiments the oligomeric compounds of the invention can comprise at least 90% sequence identity and in some embodiments can comprise at least 95% sequence identity to to a small non-coding RNA or a region thereof.

Oligomeric compounds, or portions thereof, may have a defined percent identity to a SEQ ID NO, or a compound having a specific ISIS number. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO.) It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (i.e., one base replaced with another) versions of the oligonucleotides taught herein fall within the scope of the invention. Percent identity is calculated according to the number of bases that are identical to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. In the context of the invention, the full length of the modified sequence may constitute a single portion.

"Targeting" an oligomeric compound to a particular nucleic acid molecule, in the context of this invention, can be a multistep process. The process usually begins with the identification of a target nucleic acid whose levels, expression or function is to be modulated. This target nucleic acid may be, for example, a small non-coding RNA or its precursor (including a pri-miRNA), or a nucleic acid molecule from an infectious agent.

The targeting process usually also includes determination of at least one target region, segment, or site within the target nucleic acid for the interaction to occur such that the desired effect, e.g., modulation of levels, expression or function, will result. Within the context of the present invention, the term "region" is defined as a portion of the target nucleic acid having at least one identifiable sequence, structure, function, or characteristic. Within regions of target nucleic acids are segments. "Segments" are defined as smaller or sub-portions of regions within a target nucleic acid. "Sites," as used in the present invention, are defined as specific positions within a target nucleic acid. The terms region, segment, and site can also be used to describe an oligomeric compound of the invention such as for example a gapped oligomeric compound having three separate segments.

Target regions include, but are not limited to, the following regions of a pri-miRNA: the mature miRNA, the Drosha recognition region, the Drosha cleavage site, the stem region of a predicted hairpin, or the loop region of a predicted hairpin. A pri-miRNA target region may be contained within a polycistronic pri-miRNA transcript or a monocistronic pri-miRNA transcript. An miRNA gene may be found as a solitary transcript, or it may be found within a 5' untranslated region (5'UTR), within in an intron, or within a 3' untranslated region (3'UTR) of a gene. It is understood that a miRNA transcript derived from a miRNA gene transcript (i.e. a transcript which does not encode for a translated protein), or an miRNA transcript derived from an miRNA gene found within 5'UTR, a 3'UTR, or an intron, are suitable target regions.

As exemplified herein, non-coding RNA genes and their products, including polycistronic miRNA genes, polycistronic pri-miRNAs, monocistronic pri-miRNAs, pre-miRNAs, and miRNAs, are also suitable targets of the compounds of the invention.

The locations on the target nucleic acid to which compounds and compositions of the invention hybridize are herein referred to as "suitable target segments." As used herein the term "suitable target segment" is defined as at least an 8-nucleobase portion of a target region to which an oligomeric compound is targeted. Suitable target segments additionally include 9-, 10-, 11-, 12-, 13-, 14-, 15-, 16-, 17-, 18, 19, 20, or 21 nucleobase portions of a target region to which an oligomeric compound is targeted.

Once one or more targets, target regions, segments or sites have been identified, oligomeric compounds are designed to be sufficiently complementary to the target, i.e., hybridize sufficiently well and with sufficient specificity, to give the desired effect. The desired effect may include, but is not limited to modulation of the levels, expression or function of the target.

In some embodiments of the invention, the oligomeric compounds are designed to exert their modulatory effects via mimicking or targeting small non-coding RNAs associated with cellular factors that affect gene expression, more specifically those involved in RNA or DNA modifications. These modifications include, but are not limited to, posttranscriptional or chromosomal modifications such as methylation, acetylation, pseudouridylation or amination.

The oligomeric compounds of the invention may be in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or proteins to effect modulation of the levels, expression or function of the target nucleic acid.

One non-limiting example of such a protein is the Drosha RNase III enzyme. Drosha is a nuclear enzyme that processes long primary RNA transcripts (pri-miRNAs) from approximately 70 to 450 nucleotides in length into pre-miRNAs (from about 50 to about 80 nucleotides in length) which are exported from the nucleus to encounter the human Dicer enzyme which then processes pre-miRNAs into miRNAs. It is believed that, in processing the pri-miRNA into the pre-miRNA, the Drosha enzyme cuts the pri-miRNA at the base of the mature miRNA, leaving a 2-nt 3' overhang (Lee, et al., Nature, 2003, 425, 415-419). The 3' two-nucleotide overhang structure, a signature of RNaseIII enzymatic cleavage, has been identified as a critical specificity determinant in targeting and maintaining small RNAs in the RNA interference pathway (Murchison, et al., Curr. Opin. Cell Biol., 2004, 16, 223-9).

A further non-limiting example involves the enzymes of the RISC complex. Use of the RISC complex to effect cleavage of RNA targets thereby greatly enhances the efficiency of oligonucleotide-mediated inhibition of gene expression. Similar roles have been postulated for other ribonucleases such as those in the RNase III and ribonuclease L family of enzymes.

Oligonucleotide Synthesis

Oligomeric compounds and phosphoramidites are made by methods well known to those skilled in the art. Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition, specific protocols for the synthesis of oligomeric compounds of the invention are illustrated in the examples below.

RNA oligomers can be synthesized by methods disclosed herein or purchased from various RNA synthesis companies such as for example Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

Methods of isolation and analysis of oligonucleotides are well known in the art. A 96-well plate format is particularly useful for the synthesis, isolation and analysis of oligonucleotides.

RNA Synthesis

Methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedron Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

Oligonucleotide Modifications

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers generally to an oligomer or polymer of ribonucleic acid (RNA) or deoxyribonucleic acid (DNA). This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkenyl, sulfamate; methyleneimino, methylenehydrazino, sulfonate, sulfonamide, amide and others having mixed N, O, S and CH$_2$ component parts. In addition to the modifications described above, the nucleosides of the oligomeric compounds of the invention can have a variety of other modifications.

Modified Internucleoside Linkages

Specific examples of oligomeric compounds useful in this invention include oligonucleotides containing modified, i.e. non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases. Oligomeric compounds of the invention can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

A suitable phosphorus-containing modified internucleoside linkage is the phosphorothioate internucleoside linkage. Additional modified oligonucleotide backbones (internucleoside linkages) containing a phosphorus atom therein include, for example, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In other embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— (known as a methylene(methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). The MMI type internucleoside linkages are disclosed in the above referenced U.S. Pat. No. 5,489,677. Amide internucleoside linkages are disclosed in the above referenced U.S. Pat. No. 5,602,240.

Modified oligonucleotide backbones (internucleoside linkages) that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Another group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA oligomeric compounds include, but are not limited to, U.S. Pat. Nos. 5,539,082; 5,714,331; and 5,719,262, each of which is herein incorporated by reference. Teaching of PNA oligomeric compounds can be found in Nielsen et al., *Science*, 1991, 254, 1497-1500. PNA has been modified to incorporate numerous modifications since the basic PNA structure was first prepared.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A suitable class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, Biochemistry, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Another class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase resulting in cleavage of the target RNA strand.

Modified Sugar Moieties

Oligomeric compounds of the invention may also contain one or more modified or substituted sugar moieties. The base units are maintained for hybridization with an appropriate nucleic acid target compound. Sugar modifications may impart nuclease stability, binding affinity or some other beneficial biological property to the oligomeric compounds. Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. These oligomeric compounds comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Some oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification that imparts increased nuclease resitance and a very high binding affinity to nucleotides is the 2-methoxyethoxy(2'-MOE, 2'-OCH$_2$CH$_2$OCH$_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Oligomeric compounds having 2'-MOE modifications are capable of inhibiting miRNA activity in vitro and in vivo (Esau et al., J. Biol. Chem., 2004, 279, 52361-52365; U.S. Application Publication No. 2005/0261218).

Additional modifications include 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other sugar substituent groups include methoxy(—O—$CH_3$), aminopropoxy(—$OCH_2CH_2CH_2NH_2$), allyl(—$CH_2$—CH=$CH_2$), —O-allyl(—O—$CH_2$—CH=$CH_2$) and fluoro (F). 2'-Sugar substituent groups may be in the arabino (up) position or ribo (down) position. One 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative substituents groups are disclosed in U.S. Pat. No. 6,172,209 entitled "Capped 2'-Oxyethoxy Oligonucleotides," hereby incorporated by reference in its entirety.

Representative cyclic substituent groups are disclosed in U.S. Pat. No. 6,271,358 entitled "RNA Targeted 2'-Oligomeric compounds that are Conformationally Preorganized," hereby incorporated by reference in its entirety.

Particular sugar substituent groups include $O((CH_2)_nO)_m$ $CH_3$, $O(CH_2)_nOCH_3$, $O(CH_2)_nNH_2$, $O(CH_2)_nCH_3$, $O(CH_2)_n$ $ONH_2$, and $O(CH_2)_nON((CH_2)_nCH_3))_2$, where n and m are from 1 to about 10.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Another group of modifications includes nucleosides having sugar moieties that are bicyclic thereby locking the sugar conformational geometry. Such modifications may impart nuclease stability, binding affinity or some other beneficial biological property to the oligomeric compounds. The most studied of these nucleosides is a bicyclic sugar moiety having a 4'-$CH_2$—O-2' bridge. As can be seen in the structure below the 2'-O— has been linked via a methylene group to the 4' carbon. This bridge attaches under the sugar as shown forcing the sugar ring into a locked 3'-endo conformation geometry. The alpha-L nucleoside has also been reported wherein the linkage is above the ring and the heterocyclic base is in the alpha rather than the beta-conformation (see U.S. Patent Application Publication No.: Application 2003/0087230). The xylo analog has also been prepared (see U.S. Patent Application Publication No.: 2003/0082807). The preferred bridge for a locked nucleic acid (LNA) is 4'-(—$CH_2$—)$_n$-O-2' wherein n is 1 or 2. The literature is confusing when the term locked nucleic acid is used but in general locked nucleic acids refers to n=1, ENA™ refers to n=2 (Kaneko et al., U.S. Patent Application Publication No.: US 2002/0147332, Singh et al., Chem. Commun., 1998, 4, 455-456, also see U.S. Pat. Nos. 6,268,490 and 6,670,461 and U.S. Patent Application Publication No.: US 2003/0207841). However the term locked nucleic acids can also be used in a more general sense to describe any bicyclic sugar moiety that has a locked conformation.

ENA™ along with LNA (n=1) have been studied more than the myriad of other analogs. Oligomeric compounds incorporating LNA and ENA analogs display very high duplex thermal stabilities with complementary DNA and RNA (Tm=+3 to +10 C), stability towards 3'-exonucleolytic degradation and good solubility properties.

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Some oligonucleotide mimetics have been prepared to incude bicyclic and tricyclic nucleoside analogs (see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

Another oligonucleotide mimetic has been reported wherein the furanosyl ring has been replaced by a cyclobutyl moiety.

Nucleobase Modifications

Oligomeric compounds of the invention may also contain one or more nucleobase (often referred to in the art simply as "base") modifications or substitutions which are structurally distinguishable from, yet functionally interchangeable with, naturally occurring or synthetic unmodified nucleobases. Such nucleobase modifications may impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov, et al., *Nucleosides and Nucleotides*, 1997, 16, 1837-1846), 1,3-diazaphenothiazine-2-one ($R_{10}$=S, $R_{11}$-$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$-$R_{14}$=F) (Wang, J.; Lin, K.-Y., Matteucci, M. Tetrahedron Lett. 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold ($R_{10}$=O, $R_{11}$=—O—($CH_2$)$_2$—$NH_2$, $R_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. No. 6,028,183, and U.S. Pat. No. 6,007,992, the contents of both are incorporated herein in their entirety.

The enhanced binding affinity of the phenoxazine derivatives together with their sequence specificity makes them valuable nucleobase analogs for the development of more potent antisense-based drugs. In fact, promising data have been derived from in vitro experiments demonstrating that heptanucleotides containing phenoxazine substitutions can activate RNaseH, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

Certain nucleobase substitutions, including 5-methylcytosinse substitutions, are particularly useful for increasing the binding affinity of the oligonucleotides of the invention. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Conjugated Oligomeric Compounds

One substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

Furthermore, the oligomeric compounds of the invention can have one or more moieties bound or conjugated, which facilitates the active or passive transport, localization, or compartmentalization of the oligomeric compound. Cellular localization includes, but is not limited to, localization to within the nucleus, the nucleolus, or the cytoplasm. Compartmentalization includes, but is not limited to, any directed movement of the oligonucleotides of the invention to a cellular compartment including the nucleus, nucleolus, mitochondrion, or imbedding into a cellular membrane. Furthermore, the oligomeric compounds of the invention comprise one or more conjugate moieties which facilitate posttranscriptional modification.

The oligomeric compounds of the invention may also be conjugated to active drug substances, for example: aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. For double-stranded oligomeric compounds, the cap may be present at either or both termini of either strand. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Synthesis of Chimeric Oligonucleotides

In preferred embodiments, oligomeric compounds of the invention are "uniformly modified", i.e., each nucleotide position bears a non-naturally occurring internucleoside linkage, sugar moiety and/or nucleobase. The present invention further encompasses "positionally modified" oligomeric compounds, in which one or more of the aforementioned modifications is incorporated in a single oligomeric compound (e.g. each nucleotide within an oligonucleotide may contain a different modification, the same modification, or be unmodified) or even at a single monomeric subunit such as a nucleoside (e.g. a nucleoside may contain both a sugar modification and a base modification) within a oligomeric compound. In one non-limiting example, a preferred oligomeric compound is modified such that each sugar moiety is a 2'-MOE nucleotide, each internucleoside linkage is a phosphorothioate linkage, and each cytosine is a 5-methyl cytosine. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, an oligomeric compound may be designed to comprise a region that serves as a substrate for RNase H. RNase H is a cellular endonuclease which cleaves the RNA strand of an RNA:DNA duplex. Activation of RNase H by an oligomeric compound having a cleavage region, therefore, results in cleavage of the RNA target, thereby enhancing the efficiency of the oligomeric compound. Consequently, comparable results can often be obtained with shorter oligomeric compounds having substrate regions when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide mimics, oligonucleotide analogs, oligonucleosides and/or oligonucleotide mimetics as described above. Such oligomeric compounds have also been referred to in the art as hybrids, hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers." Methods of synthesizing chimeric oligonucleotides are well known in the art.

Nucleotides, both native and modified, have a certain conformational geometry which affects their hybridization and affinity properties. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as, but not limited to, antisense mechanisms, including RNase H-mediated and RNA interference mechanisms, as these mechanisms involved the hybridization of a synthetic sequence strand to an RNA target strand. In the case of RNase H, effective inhibition of the mRNA requires that the antisense sequence achieve at least a threshold of hybridization.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is also correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but are not limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds designed to act as triggers of RNAi having one or more nucleosides modified in such a way as to favor a C3'-endo type conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.)

The conformation of modified nucleosides and their oligomers can be estimated by various methods such as molecular dynamics calculations, nuclear magnetic resonance spectroscopy and CD measurements. Hence, modifications predicted to induce RNA-like conformations (A-form duplex geometry in an oligomeric context), are useful in the oligomeric compounds of the present invention. The synthesis of modified nucleosides amenable to the present invention are known in the art (see for example, Chemistry of Nucleosides and Nucleotides Vol 1-3, ed. Leroy B. Townsend, 1988, Plenum Press.)

In one aspect, the present invention is directed to oligomeric compounds that are designed to have enhanced properties compared to native RNA. One method to design optimized or enhanced oligomeric compounds involves each nucleoside of the selected sequence being scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position of a double-stranded sequence or sequences. Other modifications considered are internucleoside linkages, conjugate groups, substitute sugars or bases, substitution of one or more nucleosides with nucleoside mimetics and any other modification that can enhance the desired property of the oligomeric compound.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one, or about 1 to about 3 hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. The number of carbon atoms can vary from 1 to about 12, from 1 to about 6, and the total number of ring members varies from three to about 15, or from about 3 to about 8. Suitable ring heteroatoms are N, O and S. Suitable heterocycloalkyl groups include, but are not limited to, morpholino, thiomorpholino, piperidinyl, piperazinyl, homopiperidinyl, homopiperazinyl; homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. Especially suitable aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. The ring system can contain about 1 to about 4 rings. The number of carbon atoms can vary from 1 to about 12, from 1 to about 6, and the total number of ring members varies from three to about 15, or from about 3 to about 8. Suitable ring heteroatoms are N, O and S. Suitable hetaryl moieties include, but are not limited to, pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl(hetaryl and alkyl), aralkyl(aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo(halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc. In all the preceding formulae, the squiggle (~) indicates a bond to an oxygen or sulfur of the 5'-phosphate.

Phosphate protecting groups include those described in U.S. Pat. Nos. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

Screening Oligomeric Compounds

Screening methods for the identification of effective modulators of small non-coding RNAs, including pri-miRNAs, are also comprehended by the instant invention and comprise the steps of contacting a small non-coding RNA, or portion thereof, with one or more candidate modulators, and selecting for one or more candidate modulators which decrease or increase the levels, expression or alter the function of the small non-coding RNA. As described herein, the candidate modulator can be an oligomeric compound targeted to a pri-miRNA, or any portion thereof, including the mature miRNA, the Drosha recognition region, the Drosha cleavage region, the stem of the hairpin, or the loop of the hairpin. Candidate modulators further include small molecule compounds that bind to structured regions of small non-coding RNAs, such as structured regions within pri-miRNAs. Once it is shown that the candidate modulator or modulators are capable of modulating (e.g. either decreasing or increasing) the levels, expression or altering the function of the small non-coding RNA, the modulator may then be employed in further investigative studies, or for use as a target validation, research, diagnostic, or therapeutic agent in accordance with the present invention. In one embodiment, the candidate modulator is screened for its ability to cause the accumulation of pri-miRNA levels.

As described herein, oligomeric compounds are further used to identify Drosha recognition regions.

Screening methods for the identification of small non-coding RNA mimics are also within the scope of the invention. Screening for small non-coding RNA modulators or mimics can also be performed in vitro, ex vivo, or in vivo by contacting samples, tissues, cells or organisms with candidate modulators or mimics and selecting for one or more candidate modulators which show modulatory effects.

Design and Screening of Duplexed Oligomeric Compounds

In screening and target validation studies, oligomeric compounds of the invention can be used in combination with their respective complementary strand oligomeric compound to form stabilized double-stranded (duplexed) oligonucleotides. In accordance with the present invention, a series of duplexes comprising the oligomeric compounds of the present invention and their complements can be designed to target a small non-coding RNA. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in some embodiments, both strands of the duplex would be complementary over the central nucleobases, each having overhangs at one or both termini, as described supra.

In some embodiments, a duplex comprising an antisense strand having the sequence CGAGAGGCGGACGGGACCG (SEQ ID NO: 1) may be prepared with blunt ends (no single stranded overhang) as shown:

```
cgagaggcggacgggaccg   Antisense Strand (SEQ ID NO: 1)
|||||||||||||||||||
gctctccgcctgccctggc   Complement (SEQ ID NO: 2)
```

In other embodiments, a duplex comprising an antisense strand having the sequence CGAGAGGCGGACGGGACCG (SEQ ID NO: 1), having a two-nucleobase overhang of deoxythymidine (dT) and its complement sense strand may be prepared with overhangs as shown:

```
                        Antisense
  cgagaggcggacgggaccgTT  Strand (SEQ ID NO: 3)
  |||||||||||||||||||
TTgctctccgcctgccctggc    Complement Sense
                         Strand (SEQ ID NO: 4)
```

These sequences are shown to contain thymine (T) but one of skill in the art will appreciate that thymine (T) is generally replaced by uracil (U) in RNA sequences. RNA strands of the duplex can be synthesized by methods disclosed herein or purchased from Dharmacon Research Inc. (Lafayette, Colo.).

Diagnostics, Drug Discovery and Therapeutics

The oligomeric compounds and compositions of the present invention can additionally be utilized for research, drug discovery, kits and diagnostics, and therapeutics.

For use in research, oligomeric compounds of the present invention are used to interfere with the normal function of the nucleic acid molecules to which they are targeted. Expression patterns within cells or tissues treated with one or more oligomeric compounds or compositions of the invention are compared to control cells or tissues not treated with the compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

For use in drug discovery, oligomeric compounds of the present invention are used to elucidate relationships that exist between small non-coding RNAs, genes or proteins and a disease state, phenotype, or condition. These methods include detecting or modulating a target comprising contacting a sample, tissue, cell, or organism with the oligomeric compounds and compositions of the present invention, measuring the levels of the target and/or the levels of downstream gene products including mRNA or proteins encoded thereby, a related phenotypic or chemical endpoint at some time after treatment, and optionally comparing the measured value to an untreated sample, a positive control or a negative control. These methods can also be performed in parallel or in combination with other experiments to determine the function of unknown genes for the process of target validation or to determine the validity of a particular gene product as a target for treatment or prevention of a disease.

For use in kits and diagnostics, the oligomeric compounds and compositions of the present invention, either alone or in combination with other compounds or therapeutics, can be used as tools in differential and/or combinatorial analyses to elucidate expression patterns of a portion or the entire complement of non-coding or coding nucleic acids expressed within cells and tissues.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder presenting conditions that can be treated, ameliorated, or improved by modulating the expression of a selected small non-coding target nucleic acid is treated by administering the compounds and compositions. For example, in one non-limiting embodiment, the methods comprise the step of administering to or contacting the animal, an effective amount of a modulator or mimic to treat, ameliorate or improve the conditions associated with the disease or disorder. The compounds of the present invention effectively modulate the activity or function of the small non-coding RNA target or inhibit the expression or levels of the small non-coding RNA target. In preferred embodiments, the small non-coding RNA target is a polycistronic pri-miRNA, a monocistronic pri-miRNA, a pre-miRNA, or a miRNA. In additional embodiments, the small non-coding RNA target is a single member of a miRNA family. Alternatively, two or more members of an miRNA family are selected for modulation. In a further embodiment, the small non-coding RNA target is a selectively processed miRNA. In one embodiment, the level, activity or expression of the target in an animal is inhibited by about 10%. In another embodiment the level, activity or expression of a target in an animal is inhibited by about 30%. Further, the level, activity or expression of a target in an animal is inhibited by 50% or more, by 60% or more, by 70% or more, by 80% or more, by 90% or more, or by 95% or more. In another embodiment, the present invention provides for the use of a compound of the invention in the manufacture of a medicament for the treatment of any and all conditions associated with miRNAs and miRNA families.

The reduction of target levels may be measured in serum, adipose tissue, liver or any other body fluid, tissue or organ of the animal known to contain the small non-coding RNA or its precursor. Further, the cells contained within the fluids, tissues or organs being analyzed contain a nucleic acid molecule of a downstream target regulated or modulated by the small non-coding RNA target itself.

Compositions and Methods for Formulating Pharmaceutical Compositions

The present invention also include pharmaceutical compositions and formulations that include the oligomeric compounds, small non-coding RNAs and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The oligomeric compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

The oligomeric compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. Suitable examples include, but are not limited to, sodium and postassium salts.

In some embodiments, an oligomeric compound can be administered to a subject via an oral route of administration. The subject may be a mammal, such as a mouse, a rat, a dog, a guinea pig, or a non-human primate. In some embodiments, the subject may be a human or a human patient. In certain embodiments, the subject may be in need of modulation of the level or expression of one or more pri-miRNAs as discussed in more detail herein. In some embodiments, compositions for administration to a subject will comprise modified oligonucleotides having one or more modifications, as described herein.

Cell Culture and Oligonucleotide Treatment

The effects of oligomeric compounds on target nucleic acid expression or function can be tested in any of a variety of cell types provided that the target nucleic acid is present at measurable levels. This can be readily determined by methods routine in the art, for example Northern blot analysis, ribonuclease protection assays, or real-time PCR. Cell types used for such analyses are available from commerical vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to: T-24 cells, A549 cells, normal human mammary epithelial cells (HMECs), MCF7 cells, T47D cells, BJ cells, B16-F10 cells, human vascular endothelial cells (HUVECs), human neonatal dermal fibroblast (NHDF) cells, human embryonic keratinocytes (HEK), 293T cells, HepG2, human preadipocytes, human differentiated adipocytes (preapidocytes differentiated according to methods known in the art), NT2 cells (also known as NTERA-2 cl.D1), and HeLa cells.

Treatment with Antisense Oligomeric Compounds

In general, when cells reach approximately 80% confluency, they are treated with oligomeric compounds of the invention. Oligomeric compounds are introduced into cells using the cationic lipid transfection reagent LIPOFECTIN® (Invitrogen, Carlsbad, Calif.). Oligomeric compounds are mixed with LIPOFECTIN® in OPTI-MEM® 1 (Invitrogen, Carlsbad, Calif.) to achieve the desired final concentration of oligomeric compound and LIPOFECTIN®. Before adding to cells, the oligomeric compound, LIPOFECTIN® and OPTI-MEM® 1 are mixed thoroughly and incubated for approximately 0.5 hrs. The medium is removed from the plates and the plates are tapped on sterile gauze. Each well of a 96-well plate is washed with 150 µl of phosphate-buffered saline or Hank's balanced salt solution. Each well of a 24-well plate is washed with 250 µL of phosphate-buffered saline or Hank's balanced salt solution. The wash buffer in each well is replaced with 100 µL or 250 µL of the oligomeric compound/OPTI-MEM® 1/LIPOFECTIN® cocktail for 96-well or 24-well plates, respectively. Untreated control cells receive LIPOFECTIN® only. The plates are incubated for approximately 4 to 7 hours at 37° C., after which the medium is removed and the plates are tapped on sterile gauze. 100 µl or 1 mL of full growth medium is added to each well of a 96-well plate or a 24-well plate, respectively. Cells are harvested 16-24 hours after oligonucleotide treatment, at which time RNA can be isolated and target reduction measured by real-time PCR, or other phenotypic assays performed. In general, data from treated cells are obtained in triplicate, and results presented as an average of the three trials.

Alternatively, cells are transfected using LIPOFECTAMINE® (Invitrogen, Carlsbad, Calif.). When cells reached 65-75% confluency, they are treated with oligonucleotide. Oligonucleotide is mixed with LIPOFECTAMINE® in OPTI-MEM® 1 reduced serum medium (Invitrogen, Carlsbad, Calif.) to achieve the desired concentration of oligonucleotide and a LIPOFECTAMINE® concentration of ranging from 2 to 12 µg/mL per 100 nM oligonucleotide. This transfection mixture is incubated at room temperature for approximately 0.5 hours. For cells grown in 96-well plates, wells are washed once with 100 µL OPTI-MEM® 1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh medium. Cells were harvested 16-24 hours after oligonucleotide treatment.

In some embodiments, cells are transiently transfected with oligomeric compounds of the instant invention. In some embodiments, cells are transfected and selected for stable expression of an oligomeric compound of the instant invention.

The concentration of oligonucleotide used varies from cell line to cell line. Methods to determine the optimal oligonucleotide concentration for a particular cell line are well known in the art. For example, the cells are treated with a positive control oligonucleotide targeting a gene such as H-ras, at a range of concentrations. Controls may be unmodified, uniformly modified, or chimeric oligomeric compounds. The concentration of positive control oligonucleotide that results in, for example, 80% inhibition of the control target RNA is then be utilized as the screening concentration for new oligonucleotides in subsequent experiments for that cell line. If 80% inhibition is not achieved, the lowest concentration of positive control oligonucleotide that results in 60% inhibition of target expression or function is then utilized as the oligonucleotide screening concentration in subsequent experiments for that cell line. The concentrations of oligonucleotides used herein can range from 1 nM to 300 nM.

Analysis of Oligonucleotide Inhibition of a Target Levels or Expression

Modulation of target levels or expression can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Additional examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression)(Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904), and mass spectrometry methods (To, Comb. Chem. High Throughput Screen, 2000, 3, 235-41).

RNA Isolation

RNA is prepared from cell lines such as HeLa, NT2, T-24, and A549 using methods well known in the art, for example, using the TRIZOL® (Invitrogen, Carlsbad, Calif.) according to the manufacturer's recommended protocols. Briefly, cell monolayers are washed twice with cold PBS, and cells are lysed using TRIZOL® (Invitrogen, Carlsbad, Calif.) at a volume of 1 mL per 10 $cm^2$ culture dish surface area, and total RNA is prepared according to the TRIZOL® protocol.

Quantitative Real-Time PCR Analysis of Target RNA Levels

Quantitation of target RNA levels is accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene (or RNA) target quantities obtained by real time PCR are normalized using either the expression level of a gene whose expression is constant, such as GAPDH, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent (Molecular Probes, Inc. Eugene, Oreg.). Methods of RNA quantification by RIBOGREEN® are taught in Jones, L. J., et al, (Analytical Biochemistry, 1998, 265, 368-374).

In this assay, 170 μL of RIBOGREEN® working reagent (RIBOGREEN® reagent diluted 1:350 in 10 mM Tris-HCl, 1 mM EDTA, pH 7.5) is pipetted into a 96-well plate containing 30 μL purified, cellular RNA. The plate is read in a CYTOFLUOR® 4000 (PE Applied Biosystems) with excitation at 485 nm and emission at 530 nm.

Probes and primers are designed to hybridize to the target sequence. Methods for designing real-time PCR probes and primers are well known in the art, and may include the use of software such as PRIMER EXPRESS® Software (Applied Biosystems, Foster City, Calif.).

Northern Blot Analysis of Target RNA Levels

Northern blot analysis is performed according to routine procedures known in the art. Fifteen to twenty micrograms of total RNA is fractionated by electrophoresis through 10% acrylamide urea gels using a TBE buffer system (Invitrogen). RNA is transferred from the gel to HYBOND™-N+ nylon membranes (Amersham Pharmacia Biotech, Piscataway, N.J.) by electroblotting in an Xcell SURELOCK™ Minicell (Invitrogen, Carlsbad, Calif.). Membranes are fixed by UV cross-linking using a STRATALINKER® UV Crosslinker 2400 (Stratagene, Inc, La Jolla, Calif.) and then probed using RAPID HYB™ buffer solution (Amersham) using manufacturer's recommendations for oligonucleotide probes.

A target specific DNA oligonucleotide probe with the sequence is used to detect the RNA of interest. Probes used to detect miRNAs are synthesized by commercial vendors such as IDT (Coralville, Iowa). The probe is 5' end-labeled with T4 polynucleotide kinase with ($\gamma$-$^{32}$P) ATP (Promega, Madison, Wis.). To normalize for variations in loading and transfer efficiency membranes are stripped and re-probed for U6 RNA. Hybridized membranes are visualized and quantitated using a STORM® 860 PHOSPHORIMAGER® System and IMAGEQUANT® Software V3.3 (Molecular Dynamics, Sunnyvale, Calif.).

Analysis of Protein Levels

Protein levels of a downstream target modulated or regulated by a small non-coding RNA can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Phenotypic Assays

Once modulators are designed or identified by the methods disclosed herein, the oligomeric compounds are further investigated in one or more phenotypic assays, each having measurable endpoints predictive or suggestive of efficacy in the treatment, amelioration or improvement of physiologic conditions associated with a particular disease state or condition.

Phenotypic assays, kits and reagents for their use are well known to those skilled in the art and are herein used to investigate the role and/or association of a target in health and disease. Representative phenotypic assays include cell cycle assays, apoptosis assays, angiogenesis assays (e.g. endothelial tube formation assays, angiogenic gene expression assays, matrix metalloprotease activity assays), adipocyte assays (e.g. insulin signaling assays, adipocyte differentiation assays), inflammation assays (e.g. cytokine signaling assays, dendritic cell cytokine production assays); examples of such assays are readily found in the art (e.g., U.S. Application Publication No. 2005/0261218, which is hereby incorporated by reference in its entirety). Additional phenotypic assays include those that evaluate differentiation and dedifferentiation of stem cells, for example, adult stem cells and embryonic stem cells; protocols for these assays are also well known in the art (e.g. Turksen, Embryonic Stem Cells: Methods and Protocols, 2001, Humana Press; Totowa, N.J.; Klug, Hematopoietic Stem Cell Protocols, 2001, Humana Press, Totowa, N.J.; Zigova, Neural Stem Cells: Methods and Protocols, 2002, Humana Press, Totowa, N.J.).

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, GENBANK® accession numbers, and the like) cited in the present application is specifically incorporated herein by reference in its entirety.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to routine methods, such as those described in Maniatis et al., Molecular Cloning—A Laboratory Manual, 2nd ed., Cold Spring Harbor Press (1989), using commercially available reagents, except where otherwise noted.

EXAMPLES

Example 1

Effects of Oligomeric Compounds on Expression of Pri-miR-NAs

As described herein, pri-miRNAs, often hundreds of nucleotides in length, are processed by a nuclear enzyme in the RNase III family known as Drosha, into approximately 70 nucleotide-long pre-miRNAs (also known as stem-loop structures, hairpins, pre-miRs or foldback miRNA precursors), and pre-miRNAs are subsequently exported from the nucleus to the cytoplasm, where they are processed by human Dicer into double-stranded miRNAs, which are subsequently processed by the Dicer RNase into mature miRNAs. It is believed that, in processing the pri-miRNA into the pre-miRNA, the Drosha enzyme cuts the pri-miRNA at the base of the mature miRNA, leaving a 2-nucleotide 3' overhang (Lee, et al., Nature, 2003, 425, 415-419). The 3' two-nucleotide overhang structure, a signature of RNaseIII cleavage, has been identified as a critical specificity determinant in targeting and maintaining small RNAs in the RNA interference pathway (Murchison, et al., Curr. Opin. Cell Biol., 2004, 16, 223-9).

The oligomeric compounds of the present invention are believed to disrupt pri-miRNA and/or pre-miRNA structures, and sterically hinder Drosha and/or Dicer cleavage, respectively. Additionally, oligomeric compounds capable of binding to the mature miRNA are believed to prevent the RISC-mediated binding of a miRNA to its mRNA target, either by degradation or steric occlusion of the miRNA.

The levels of pri-miR-15a were compared in HepG2 cells treated with a series of chimeric oligomeric compounds, targeting and spanning the entire length of pri-miR-15a; these compounds are shown in Table 1, below. The compounds were designed using publicly available sequence information (the complement of nucleotides 31603159 to 31603468 of GENBANK® Accession number NT_024524.13, deposited with GENBANK® on Oct. 7, 2003). Each chimeric oligomeric compound is 20 nucleotides in length, composed of a central "gap" region consisting of ten 2'-deoxynucleotides, which is flanked on both sides (5' and 3' directions) by five-nucleotide "wings." These chimeric compounds having a central gap region are herein referred to as "gapmers". The wings are composed of 2'-methoxyethoxy(2'-MOE) nucleotides. The internucleoside (backbone) linkages are phosphorothioate (P=S) throughout the oligonucleotide. All cytidine residues are 5-methylcytidines. Using the transfection methods described herein, HepG2 cells were treated with 100 nM of each of these gapmer oligomeric compounds. Total RNA was isolated from HepG2 cells by lysing cells in 1 mL TRIZOL® (Invitrogen, Carlsbad, Calif.) using the manufacturer's recommended protocols. The isolated RNA was used as the substrate in the reverse transcriptase, real-time PCR assays, as described herein. Real-time PCR analysis was performed using a primer/probe set specific for pri-miR-15a to assess the effects of these compounds on levels of pri-miR-15a. ISIS 339317 (GTGTGTTTAAAAAAATAAAACCT-TGGA; SEQ ID NO.: 6) was used as the forward primer, ISIS 339318 (TGGCCTGCACCTTTTCAAA; SEQ ID NO.: 7) was used as the reverse primer, and ISIS 339319 (AAAG-TAGCAGCACATAATGGTTTGTGG; SEQ ID NO.: 8) was used as the probe. Total RNA was quantified using RIBOGREEN® RNA quantification reagent (Molecular Probes, Inc. Eugene, Oreg.), levels observed for each target are normalized to 5.8S rRNA, and values are expressed relative to the untreated control. Reduction in the levels of pri-miR-15a by these gapmer oligomeric compounds is expressed as a percentage of RNA levels in untreated control cells. Results of these experiments are described in Table 1.

TABLE 1

Effects of chimeric oligomeric compounds on expression of pri-miR-15a

| ISIS Number | SEQ ID NO | Sequence | Expression of pri-miR-15a (% UTC) |
|---|---|---|---|
| 347964 | 9 | TATAACATTGATGTAATATG | 13.7 |
| 347965 | 10 | GCTACTTTACTCCAAGGTTT | 86.0 |
| 347966 | 11 | TGCTACTTTACTCCAAGGTT | 39.2 |
| 347967 | 12 | GCACCTTTTCAAAATCCACA | 152.3 |
| 347968 | 13 | CCTGCACCTTTTCAAAATCC | 8.4 |
| 347969 | 14 | TGGCCTGCACCTTTTCAAAA | 39.5 |
| 347970 | 15 | ATATGGCCTGCACCTTTTCA | 2.2 |
| 347971 | 16 | ACAATATGGCCTGCACCTTT | 92.8 |
| 347972 | 17 | AGCACAATATGGCCTGCACC | 98.6 |
| 347973 | 18 | GGCAGCACAATATGGCCTGC | 143.3 |
| 347974 | 19 | TGAGGCAGCACAATATGGCC | 98.1 |
| 347975 | 20 | TTTTGAGGCAGCACAATATG | 9.2 |
| 347976 | 21 | TATTTTTGAGGCAGCACAAT | 73.0 |
| 347977 | 22 | TTGTATTTTTGAGGCAGCAC | 111.3 |
| 347978 | 23 | TCCTTGTATTTTTGAGGCAG | 51.1 |
| 347979 | 24 | AGATCCTTGTATTTTTGAGG | 74.9 |
| 347980 | 25 | AGATCAGATCCTTGTATTTT | 3.6 |
| 347981 | 26 | AGAAGATCAGATCCTTGTAT | N/D |
| 347982 | 27 | TTCAGAAGATCAGATCCTTG | 82.2 |
| 347983 | 28 | AAATATATTTTCTTCAGAAG | 13.0 |

From these data, it was observed that oligomeric compounds ISIS 347964, 347966, 347968, 347970, 347975, 347980 and 347983 show significant inhibition of levels of pri-miR-15a. Thus, it is possible that the antisense oligomeric compounds ISIS 347964, 347966, 347968, 347970, 347975, 347980 and 347983 bind to pri-miR-15a and/or pre-miR-15a molecules and cause their degradation and cleavage.

From these data, it was observed that oligomeric compounds ISIS 347967, 347977 and 347973 stimulated an increase of pri-miR-15a levels. It is possible that the oligomeric compounds ISIS 347967, 347977 and 347973 bind to pri-miR-15a and inhibit its processing into mature miR-15a.

In addition, uniform 2'-MOE and 2'-MOE gapmer oligomeric compounds targeting mature miR-15a-1 and mature miR-15b were transfected into T47D cells, for analysis of their effects on pri-miR-15a-1 and/or pri-miR-15b levels. The oligomeric compounds ISIS 327927 (SEQ ID NO: 29), a uniform 2'-MOE compound, and ISIS 345391 (SEQ ID NO: 29), a 2'-MOE 5-10-7 gapmer compound, both target mature miR-15b. The oligomeric compounds ISIS 327951 (SEQ ID NO: 30), a uniform 2'-MOE compound, and ISIS 345411 (SEQ ID NO: 30), a 2'-MOE 5-10-7 gapmer compound, both target mature miR-15a-1. Oligomeric compounds ISIS 129686 (CGTTATTAACCTCCGTTGAA; SEQ ID NO: 31), ISIS 129691 (ATGCATACTACGAAAGGCCG; SEQ ID NO:32), and ISIS 116847 (CTGCTAGCCTCTGGATTTGA; SEQ ID NO: 33; targeting an unrelated gene, PTEN), are not designed to target to mature miR-15b or mature miR-15-a-1, and were used as negative controls. ISIS 129686, 129691, and 116847 are phosphorothiated 2'-MOE 5-10-5 gapmers, and all cytosines are 5-methylcytosines. T47D cells (seeded in 12-well plates) were treated with these oligomeric compounds, RNA was isolated from the treated cells by lysing in 1 mL TRIZOL® (Invitrogen, Carlsbad, Calif.) and total RNA was prepared using the manufacturer's recommended protocols. To assess the effects of these compounds on pri-miR-15a and/or pri-miR-15b levels, real-time PCR analysis was performed using either the primer/probe set specific for pri-miR-15a described above, or a primer probe set specific for pri-miR-15b: ISIS 339320 (CCTACATTTTTGAGGCCTTAAAGTACTG; SEQ ID NO: 34) was used as the forward primer for the pri-miR-15b, ISIS 339321 (CAAATAATGATTCGCATCTTGACTGT; SEQ ID NO: 35) was used as the reverse primer for the pri-miR-15b, and ISIS 339322 (AGCAGCACATCATGGTTTACATGC; SEQ ID NO: 36) was used as the probe. Total RNA was quantified using RIBOGREEN® RNA quantification reagent (Molecular Probes, Inc. Eugene, Oreg.), levels observed for each target were normalized to 5.8S rRNA, and values are expressed relative to the untreated control. Inhibition of pri-miR-15a or pri-miR-15b levels upon treatment with these oligomeric compounds is was assessed and expressed as a percentage of RNA levels in untreated control cells.

Following repeated experimentation, it was observed that the uniform 2'-MOE oligomeric compounds ISIS 327927 (SEQ ID NO: 29) and ISIS 327951 (SEQ ID NO: 30), targeted to the mature miR-15b and mature miR-15a-1, respectively, each stimulate an approximately 2.5-3.5-fold increase in level of pri-miR-15a and an approximately 1.5- to 2.5-fold increase in the level of pri-miR-15b. Therefore, it is possible that ISIS 327927 and 327951 can bind to pri-miR-15a and pri-miR-15b, or their respective pre-miRNAs, and interfere with their processing into the mature miR-15a or mature miR-15b.

In accordance with the present invention, a nested series of uniform 2'-MOE oligomeric compounds were designed and synthesized to target the entire length of pri-miR-15a, using publicly available sequence information (the complement of nucleotides 31603159 to 31603468 of GENBANK® Accession number NT_024524.13, deposited with GENBANK® on Oct. 7, 2003). The compounds are shown in Table 2. Each compound is 19 nucleotides in length, composed of 2'-methoxyethoxy(2'-MOE) nucleotides and phosphorothioate (P=S) internucleoside linkages throughout the oligonucleotide. All cytidine residues are 5-methylcytidines. The compounds are analyzed for their effect on mature miRNA, pre-miRNA or pri-miRNA levels by quantitative real-time PCR; alternatively, they are used in other assays to investigate the role of miRNAs or the function of targets downstream of miRNAs.

TABLE 2

Uniform 2'-MOE PS Compounds targeting pri-miR-15a

| ISIS | SEQ ID NO | Sequence |
|---|---|---|
| 356213 | 9 | TATAACATTGATGTAATATG |
| 356214 | 10 | GCTACTTTACTCCAAGGTTT |
| 356215 | 11 | TGCTACTTTACTCCAAGGTT |
| 356216 | 12 | GCACCTTTTCAAAATCCACA |
| 356217 | 13 | CCTGCACCTTTTCAAAATCC |
| 356218 | 14 | TGGCCTGCACCTTTTCAAAA |
| 356219 | 15 | ATATGGCCTGCACCTTTTCA |
| 356220 | 16 | ACAATATGGCCTGCACCTTT |
| 356221 | 17 | AGCACAATATGGCCTGCACC |
| 356222 | 18 | GGCAGCACAATATGGCCTGC |
| 356223 | 19 | TGAGGCAGCACAATATGGCC |
| 356224 | 20 | TTTTGAGGCAGCACAATATG |
| 356225 | 21 | TATTTTTGAGGCAGCACAAT |
| 356226 | 22 | TTGTATTTTTGAGGCAGCAC |
| 356227 | 23 | TCCTTGTATTTTTGAGGCAG |
| 356228 | 24 | AGATCCTTGTATTTTTGAGG |
| 356229 | 25 | AGATCAGATCCTTGTATTTT |
| 356230 | 26 | AGAAGATCAGATCCTTGTAT |
| 356231 | 27 | TTCAGAAGATCAGATCCTTG |
| 356232 | 28 | AAATATATTTTCTTCAGAAG |

Using the reverse transcriptase and real-time PCR methods described, the levels of pri-miR-15a were compared in T47D cells treated with the nested series of uniform 2'-MOE oligomeric compounds, targeting and spanning the entire length of pri-miR-15a. ISIS 356215 (SEQ ID NO:11) targets a region flanking and immediately 5' to the predicted 5' Drosha cleavage site in pri-miR-15a. ISIS 356218 (SEQ ID NO: 14) targets a region in the loop of pri-miR-15a. ISIS 356227 (SEQ ID NO: 23) targets a region flanking and immediately 3' to the predicted 3'Drosha cleavage site in pri-miR-15a. Additionally, oligomeric compound ISIS 327951 (SEQ ID NO: 30), a uniform 2'-MOE compound targeting mature miR-15a-1, was tested for comparison. Oligomeric compounds ISIS 327901 (SEQ ID NO: 38) targeting mature miR-143; ISIS 129690, (TTAGAATACGTCGCGTTATG; SEQ ID NO: 37), a phosphorothioate 5-10-5 MOE gapmer used as a universal scrambled control; and ISIS 116847 (CTGCTAGCCTCTG-GATTTGA; SEQ ID NO: 33), a uniform 5-10-5 2'-MOE gapmer targeting an unrelated gene, PTEN, were used as negative controls. Using the transfection methods described herein, T47D cells were treated with 100 nM of each of these oligomeric compounds. Total RNA was isolated by lysing cells in 1 mL TRIZOL® (Invitrogen, Carlsbad, Calif.) using the manufacturer's recommended protocols. Real-time PCR analysis was performed using a primer/probe set specific for pri-miR-15a [forward primer=ISIS 339317 (SEQ ID NO: 6), reverse primer=ISIS 339318 (SEQ ID NO: 7), and probe=ISIS 339319 (SEQ ID NO: 8)]. Total RNA was quantified using RIBOGREEN® RNA quantification reagent (Molecular Probes, Inc. Eugene, Oreg.), levels observed for each target were normalized to 5.8S rRNA, and values were expressed relative to the untreated control (UTC). Effects on expression of pri-miR-15a resulting from treatment of T47D cells with these uniform 2'-MOE oligomeric compounds is expressed as a percentage of RNA levels in untreated control cells. Results of these experiments are described in Table 3.

TABLE 3

Effects of uniform 2'-MOE oligomeric compounds on pri-miR-15a expression

| ISIS # | SEQ ID NO: | Target | % UTC |
|---|---|---|---|
| UTC | N/A | N/A | 100 |
| 129690 scrambled control | 37 | N/A | 121 |
| 327901 | 38 | miR-143 | 132 |
| 116847 | 33 | PTEN mRNA | 132 |
| 327951 | 30 | mature miR-15a-1 | 713 |
| 356213 | 9 | >100 bp upstream of mature miR-15a | 171 |
| 356215 | 11 | flanking 5' Drosha cleavage site of pri-miR-15a-1 | 1005 |
| 356216 | 12 | pri-miR-15a-1 | 503 |
| 356218 | 14 | loop of pri-miR-15a-1 | 392 |
| 356221 | 17 | pri-15a-1 | 444 |
| 356224 | 20 | pri-15a-1 | 592 |
| 356227 | 23 | flanking 3' Drosha cleavage site of pri-15a-1 | 879 |
| 356229 | 25 | pri-15a-1 | 818 |
| 356231 | 27 | pri-15a-1 | 811 |
| 356232 | 28 | pri-15a-1 | 631 |

From these data, it was observed that the uniform 2'-MOE oligomeric compounds ISIS 327927, 327951, 356215, 356216, 356218, 356221, 356224, 356227, 356229, 356231 and 356232 stimulate an increase in levels of pri-miR-15a as detected by real-time PCR. Notably, oligomeric compounds ISIS 356215 and 356227, which target the regions immediately flanking the predicted 5, and 3' Drosha cleavage sites in pri-miR-15a, respectively, were observed to stimulate the greatest increases in levels of pri-miR-15a. It is possible that these oligomeric compounds bind to pri-miR-15a and/or the respective pre-miRNA and interfere with their processing into mature miR-15a, possibly by interfering with the activity of RNase III-like enzymes such as human Dicer and/or Drosha. It is understood that such effect of oligomeric compounds may be operating not only upon regulation of miR-15a production and processing, but may also be found to regulate the production and processing of other miRNAs.

The expression levels of miR-24-2, let-7i, and let-7d were assessed in HeLa or T-24 cells treated with various uniform 2'-MOE oligomeric compounds targeting mature miRNAs (designed using publicly available mature miRNA sequences). For example, using the transfection methods previously described, HeLa cells were treated with 100 nM of the oligomeric compound ISIS 327945 (SEQ ID NO: 39) targeting mature miR-24-2. Total RNA was isolated, subjected to a reverse transcriptase reaction, and levels of the pri-miR-24-2 were analyzed by quantitative real-time PCR using a primer/probe set specific for pri-miR-24-2 [forward primer=ISIS 359358 (CCCTGGGCTCTGCCT; herein incorporated as SEQ ID NO: 40), reverse primer=ISIS 359359 (TGTACA-CAAACCAACTGTGTTTC; herein incorporated as SEQ ID NO: 41), and probe=ISIS 359360 (CGTGCCTACTGAGC; herein incorporated as SEQ ID NO: 42)]. An approximately 35-fold increase in levels of pri-miR-24-2 was observed in HeLa cells treated with the oligomeric compound ISIS 327945 as detected by real-time PCR.

Using the transfection methods previously described, HeLa cells were treated with 100 nM of the oligomeric compound ISIS 327890 (SEQ ID NO: 43) targeting the mature let-7i. Total RNA was isolated, subjected to reverse transcriptase, and levels of the let-7i pri-miRNA were analyzed by real-time PCR using a primer/probe set specific for the let-7i pri-miRNA [forward primer=ISIS 341684 (TGAGG-TAGTAGTTTGTGCTGTTGGT; herein incorporated as SEQ ID NO: 44), reverse primer=ISIS 341685 (AGGCAG-TAGCTTGCGCAGTTA; herein incorporated as SEQ ID NO: 45), and probe=ISIS 341686 (TTGTGACATTGC-CCGCTGTGGAG; herein incorporated as SEQ ID NO: 46)]. An approximately 4-fold increase in levels of pri-miR-let-7i molecule was observed in HeLa cells treated with the oligomeric compound ISIS 327890 as detected by real-time PCR.

Using the transfection methods previously described T-24 cells were treated with 100 nM of the oligomeric compound ISIS 327926 (SEQ ID NO: 47) targeting mature let-7d. Total RNA was isolated and subjected to reverse transcriptase, and levels of the let-7d pri-miRNA were analyzed by real-time PCR using a primer/probe set specific for let-7d pri-miRNA (forward primer=ISIS 341678 (CCTAGGAAGAGGTAG-TAGGTTGCA; herein incorporated as SEQ ID NO: 48), reverse primer=ISIS 341679 (CAGCAGGTCGTATAGT-TACCTCCTT; herein incorporated as SEQ ID NO: 49), and probe=ISIS 341680 (AGTTTTAGGGCAGGGATTTTGC-CCA; herein incorporated as SEQ ID NO: 50)). An approximately 1.7-fold increase in levels of let-7d pri-miRNA was observed in T-24 cells treated with the oligomeric compound ISIS 327926 as detected by real-time PCR.

Thus, treatment with uniform 2'-MOE oligomeric compounds targeting mature miRNAs resulted in the accumulation of pri-miRNA from which the mature miRNA is derived.

In one embodiment, the expression of miR-21 (noted to be expressed at high levels in HeLa cells) was assessed in cells treated with oligomeric compounds. Using the transfection methods previously described, HeLa cells were treated with 100 nM of the uniform 2'-MOE oligomeric compound ISIS 327917 (SEQ ID NO: 51) targeting mature miR-21. Total RNA was isolated by lysing cells in 1 mL TRIZOL® (Invitrogen, Carlsbad, Calif.) using the manufacturer's recommended protocols. By Northern blot analysis of total RNA from HeLa cells treated with ISIS 327917, levels of the miR-21 mature miRNA were observed to be reduced to 50% of those of untreated control cells. Furthermore, levels of pri-miR-21 were found to increase in these HeLa cells treated with the oligomeric compound ISIS 327917. Reverse transcriptase and real-time PCR analysis was also performed on RNA isolated from HeLa cells treated with ISIS 327917 using a primer/probe set specific for pri-miR-21 molecule [forward primer=ISIS 339332 (GCTGTACCACCTTGTCGGGT; herein incorporated as SEQ ID NO: 52), reverse primer=ISIS 339333 (TCGACTGGTGTTGCCATGA; herein incorporated as SEQ ID NO: 53), and probe=ISIS 339334 (CTTAT-CAGACTGATGTTGACTGTTGAAT; herein incorporated as SEQ ID NO: 54]. Total RNA was quantified using RIBOGREEN® RNA quantification reagent (Molecular Probes, Inc. Eugene, Oreg.), levels observed for the target were normalized to 5.8S rRNA, and values were expressed relative to an untreated control (UTC). ISIS 327917 was observed to stimulate an approximately 2-fold increase in levels of pri-miR-21 as detected by real-time PCR.

Thus, these data suggest that, in addition to binding the miR-21 mature miRNA and interfering with the RISC-mediated binding of miR-21 to its mRNA target, the oligomeric compound, ISIS 327917, may bind to pri-miR-21 and/or the respective pre-miRNA and interfere with processing of the mature miR-21, which results in reduction of mature miR-21 levels in HeLa cells, possibly by interfering with the activity of RNase III-like enzymes such as human Dicer or Drosha.

In accordance with the present invention, a nested series of uniform 2'-MOE oligomeric compounds were designed and synthesized to target the entire length of pri-miR-21. The oligomeric compounds were designed using publicly available sequence information (nucleotides 16571584 to 16571864 of GENBANK® Accession number NT_010783.14, deposited with GENBANK® on Oct. 7, 2003). Each compound is 20 nucleotides in length, composed of 2'-methoxyethoxy(2'-MOE) nucleotides and phosphorothioate (P=S) internucleoside linkages throughout the compound. All cytidine residues are 5-methylcytidines. The compounds are shown in Table 4. The compounds are analyzed for their effect on mature miRNA, pre-miRNA or pri-miRNA levels by quantitative real-time PCR; alternatively, they are used in other assays to investigate the role of miRNAs or the function of targets downstream of miRNAs.

TABLE 4

Uniform 2'-MOE PS Compounds targeting pri-miR-21

| ISIS Number | SEQ ID NO | Sequence |
|---|---|---|
| 358765 | 55 | ACAAGCAGACAGTCAGGCAG |
| 358766 | 56 | GGTAGGCAAAACAAGCAGAC |
| 358767 | 57 | GGAGATGTCACGATGGTAGG |
| 358768 | 58 | AGGTGGTACAGCCATGGAGA |
| 358769 | 59 | GATAAGCTACCCGACAAGGT |
| 358770 | 60 | AGTCTGATAAGCTACCCGAC |
| 358771 | 61 | CAACAGTCAACATCAGTCTG |
| 358772 | 62 | GAGATTCAACAGTGAACATC |
| 358773 | 63 | CTGGTGTTGCCATGAGATTC |
| 358774 | 64 | CATCGACTGGTGTTGCCATG |
| 358775 | 65 | ACAGCCCATCGACTGGTGTT |
| 358776 | 66 | TGTCAGACAGCCCATCGACT |
| 358777 | 67 | CCAAAATGTCAGACAGCCCA |
| 358778 | 68 | GATACCAAAATGTCAGACAG |
| 358779 | 69 | GGTCAGATGAAAGATACCAA |
| 358780 | 70 | AACATTGGATATGGATGGTC |
| 358781 | 71 | TAATGTTTAAATGAGAACAT |
| 358782 | 72 | AACAATGATGCTGGGTAATG |
| 358783 | 73 | GAGTTTCTGATTATAAACAA |
| 358784 | 74 | CGACAAGGTGGTACAGCCAT |
| 358785 | 75 | GAAAGATACCAAAATGTCAG |

Pri-miR-21 levels were compared in HeLa cells treated with this nested series of uniform 2'-MOE oligomeric compounds, targeting and spanning the entire length of pri-miR-21. ISIS 358768 (SEQ ID NO: 58) targets a region flanking the predicted 5' Drosha cleavage site in pri-miR-21. ISIS 358777 (SEQ ID NO: 67) targets a region spanning the 3' Drosha cleavage site in pri-miR21. ISIS 358779 (SEQ ID NO: 69) targets a region flanking the predicted 3 Drosha cleavage site in pri-miR-21. Additionally, oligomeric compounds ISIS 327917 (SEQ ID NO: 51), a uniform 2'-MOE compound targeting the mature miR-21 miRNA, and ISIS 345382 (TCAACATCAGTCTGATAAGCTA; SEQ ID NO: 51), a 5-10-7 phosphorothioate 2'-MOE gapmer targeting miR-21, were tested for comparison. Oligomeric compound ISIS 327863 (ACGCTAGCCTAATAGCGAGG; herein incorporated as SEQ ID NO: 76), a phosphorothioate 5-10-5 2'-MOE gapmer, was used as scrambled control. Using the transfection methods previously described, HeLa cells were treated with 100 nM of each of these oligomeric compounds. Total RNA was isolated by lysing cells in 1 mL TRIZOL® (Invitrogen, Carlsbad, Calif.) using the manufacturer's recommended protocols, and was subjected to reverse transcriptase. Real-time PCR analysis was performed using the primer/probe set specific for pri-miR-21 [forward primer=ISIS 339332 (SEQ ID N.: 52), reverse primer=ISIS 339333 (SEQ ID NO: 53), and probe=ISIS 339334 (SEQ ID NO: 54)]. Total RNA was quantified using RIBOGREEN® RNA quantification reagent (Molecular Probes, Inc. Eugene, Oreg.), levels observed for each target were normalized to 5.8S rRNA, and values were expressed relative to the untreated control (UTC). Effects on levels of pri-miR-21 resulting from treatment of HeLa cells with these uniform 2'-MOE oligomeric compounds is expressed as a percentage of RNA levels in untreated control cells. Results of these experiments are shown in Table 5.

TABLE 5

Effects of oligomeric compounds on pri-miR-21 expression

| ISIS # | SEQ ID NO: | Target | % UTC |
|---|---|---|---|
| UTC | N/A | N/A | 100 |
| 327863 gapmer control | 76 | N/A | 107 |
| 327917 Uniform 2'-MOE | 51 | mature miR-21 | 249 |
| 345382 5-10-7 2'-MOE gapmer | 51 | mature miR-21 | 119 |
| 358765 | 55 | pri-miR-21 | 133 |
| 358766 | 56 | pri-miR-21 | 142 |
| 358767 | 57 | pri-miR-21 | 248 |
| 358768 | 58 | flanking 5' Drosha cleavage site of pri-miR-21 | 987 |
| 358769 | 59 | pri-miR-21 | 265 |
| 358770 | 60 | pri-miR-21 | 250 |
| 358771 | 61 | pri-miR-21 | 181 |
| 358772 | 62 | pri-miR-21 | 245 |
| 358773 | 63 | pri-miR-21 | 148 |
| 358774 | 64 | pri-miR-21 | 104 |
| 358775 | 65 | pri-miR-21 | 222 |
| 358776 | 66 | pri-miR-21 | 367 |
| 358777 | 67 | spanning 3' Drosha cleavage site of pri-miR-21 | 536 |
| 358778 | 68 | pri-miR-21 | 503 |
| 358779 | 69 | flanking 3' Drosha cleavage | 646 |

TABLE 5-continued

Effects of oligomeric compounds on pri-miR-21 expression

| ISIS # | SEQ ID NO: | Target | % UTC |
|---|---|---|---|
| | | site of pri-miR-21 | |
| 358780 | 70 | pri-miR-21 | 269 |
| 358781 | 71 | pri-miR-21 | 122 |
| 358782 | 72 | pri-miR-21 | 155 |
| 358783 | 73 | pri-miR-21 | 133 |
| 358784 | 74 | pri-miR-21 | 358 |
| 358785 | 75 | pri-miR-21 | 257 |

From these data, it was observed that the uniform 2'-MOE oligomeric compounds ISIS 327917, 358767, 358768, 358769, 358770, 358772, 358775, 358776, 358777, 358778, 358779, 358780, 358784 and 358785 stimulate an increase in pri-miR-21 levels as detected by real-time PCR. Notably, oligomeric compounds ISIS 358768 and 358779 which target the regions flanking the predicted 5' and 3' Drosha cleavage sites, respectively, and ISIS 358777, which targets a region spanning the 3' Drosha cleavage site in pri-miR-21 were observed to stimulate the greatest increases in levels of pri-miR-21. Furthermore, treatment of HeLa cells with increasing concentrations (25, 50, 100, and 200 nM) of ISIS 358768, 358779, and 327917 was observed to result in a dose-responsive increase in pri-miR-21 levels. Thus, it is believed that these oligomeric compounds bind to pri-miR-21 and/or the respective pre-miRNA and interfere with their processing into mature miR-21, possibly by interfering with the activity of RNase III-like enzymes such as human Dicer and/or Drosha. It is understood that such effects of oligomeric compounds may be operating not only upon regulation of miR-21 production and processing, but may also be found to regulate the production and processing of other miRNAs or target nucleic acids.

In one embodiment, the oligomeric compounds ISIS 327917 (SEQ ID NO: 51), the phosphorothioate uniform 2'-MOE targeting mature miR-21; ISIS 358768 (SEQ ID NO: 58), the uniform 2'-MOE targeting pri-miR-21 which stimulated the largest increase in pri-miRNA levels by real time PCR; and ISIS 345382 (SEQ ID NO: 51), the 5-10-7 phosphorothioate 2'-MOE gapmer targeting mature miR-21 were selected for dose response studies in HeLa cells using the luciferase reporter system described in U.S. Application Publication No. 2005/0261218. ISIS 342683 (SEQ ID NO: 77), representing the scrambled nucleotide sequence of an unrelated PTP1B antisense oligonucleotide, was used as a negative control. HeLa cells expressing the pGL3-miR-21 sensor plasmid (U.S. Application Publication No. 2005/0261218) were treated with 1.9, 5.5, 16.7, and 50 nM of these oligomeric compounds, to assess the ability of oligomeric compounds to interfere with endogenous miR-21-mediated silencing of the pGL3-miR-21 sensor plasmid. The data are presented in Table 6 as percent untreated control (luciferase plasmid only, not treated with oligomeric compound) luciferase expression, normalized to pRL-CMV levels.

TABLE 6

Effects of oligomeric compounds on miR-21 miRNA-mediated inhibition of luciferase expression

| | % UTC Dose of oligomeric compound | | | |
|---|---|---|---|---|
| Treatment | 1.9 nM | 5.5 nM | 16.7 nM | 50 nM |
| 342683 Negative control | 127 | 171 | 104 | 108 |
| 327917 | 522 | 1293 | 2470 | 4534 |
| 358768 | 103 | 163 | 146 | 118 |
| 345382 | 101 | 135 | 117 | 95 |

From these data, it was observed that, at all doses, treatment of HeLa cells with ISIS 327917, the uniform 2'-MOE oligomeric compound targeting the mature miR-21 miRNA, de-repressed the expression of the luciferase reporter, in a dose-dependent fashion. Thus, ISIS 327917 reversed the silencing effect of the endogenous miR-21 miRNA, possibly by inhibiting the binding of miR-21 to its target site encoded by the pGL3-miR-21 sensor plasmid.

A similar assay using the miR-21 luciferase reporter system was performed, using oligomeric compounds ISIS 327917, ISIS 365241, ISIS 358762, ISIS 358758, and ISIS 345382; each of these compounds has the nucleobase sequence TCAACATCAGTCTGATAAGCTA (incorporated herein as SEQ ID NO: 51). Also tested was ISIS 342683 (CCTTCCCTGAAGGTTCCTCCTT, incorporated herein as SEQ ID NO: 77). ISIS 342683 is not designed to hybridize to miR sequences and was used as a negative control. ISIS 327917 and ISIS 342683 are composed of 2'-O-(2-methoxyethyl), also known as 2'-MOE, nucleotides throughout, and the internucleoside (backbone) linkages are phosphorothioate (P=S) throughout (MOE-PS). ISIS 365241 is composed of 2'-MOE nucleotides throughout, and the backbone linkages are phosphodiester (P=O) throughout (MOE-PO). ISIS 358762 is composed of 2'-O-methyl residues throughout, and the backbone linkages are phosphorothioate (P=S) throughout (MOE-PS). ISIS 358758 is composed of 2'-O-methyl residues throughout, and the backbone linkages are phosphodiester (P=O) throughout (MOE-PO). ISIS 345382 is a chimeric oligonucleotide comprised of 10 2'-deoxynucleotides, flanked on the 5'-end by 5 2'-MOE nucleotides and on the 3'-end by 7 2'-MOE nucleotides. All cytidine residues in are 5-methylcytidines.

The luciferase assay is described in U.S. application Ser. No. 10/909,125. HeLa cells were transiently transfected using LIPOFECTAMINE® 2000 transfection reagent (Invitrogen, Carlsbad, Calif.) with pRL-CMV *Renilla* luciferase plasmid (Promega, Madison, Wis.) and pGL3-miR 21 sensor for 24 hours. The pGL3-miR 21 sensor plasmid was prepared using standard cloning techniques, such as those described in U.S. Application Publication No. 2005/0261218. Cells were replated and antisense oligonucleotides targeting mature miR-21, or control antisense oligonucleotides, were transfected at doses of 1.56, 3.1, 6.25, 12.5, 25, or 50 nM for a period of six hours, after which *Renilla* luciferase activity was measured. In a similar experiment, the antisense oligonucleotides, at doses of 1.56, 3.1, 6.25, 12.5, 25, or 50 nM, were transfected simultaneously with the plasmids for a period of 24 hours, after which *Renilla* luciferase activity was measured. The oligonucleotides were evaluated for their ability to interfere with miR-21 inhibition of pGL3-miR-21 sensor luciferase expression. Each treated sample was normalized to untreated control samples.

This assay revealed that while compounds with either the 2'-MOE modification or the 2'-O-methyl modification can interfere with miR-21 activity in a dose-dependent fashion, oligomeric compounds having 2'-MOE modifications exhibited an increased ability to inhibit miR-21 activity after 24 hours of treatment, as compared to after 6 hours of treatment.

Example 2

Effect of Oligomeric Compounds Targeted to Pri-miR-15a on Levels of Related or Unrelated miRNAs Members of miRNA families are characterized by the presence of an identical seed sequence. In a further embodiment, oligomeric compounds targeted to positions of pri-miR-15a were tested for their effects on related and unrelated pri-miRs. The nucleobase sequences of members of the miR-15 family are shown in Table 7. Seed sequences within each mature miRNA sequence are underlined.

TABLE 7 miR-15 family members

| Sequence | SEQ ID NO: | miRNA | Mismatches relative to miR-15a |
|---|---|---|---|
| -<u>UAGCAGCA</u>CAUAAUGGUUUGUG--- | 98 | miR-15a | 0 |
| -<u>UAGCAGCA</u>CAUCAUGGUUUACA--- | 99 | miR-15b | 4 |
| -<u>UAGCAGCA</u>CGUAAAUAUUGGCG--- | 100 | miR-16 | 6 |
| -<u>UAGCAGCA</u>CAGAAAUAUUGGC---- | 101 | miR-195 | 6 |

Oligomeric compounds were designed using publicly available sequence (the complement of nucleotides 31603159 to 31603468 of GENBANK® Accession number NT_024524.13, deposited with GENBANK® on Oct. 7, 2003). HeLa cells were treated with the compounds in Table 8 for a period of 16 to 20 hours. RNA was isolated from the treated cells using TRIZOL® (Invitrogen, Carlsbad, Calif.) and TURBO™ DNase (Ambion, Austin, Tex.), and was subjected to a reverse transcription reaction, which was followed by real-time PCR with primer probe sets designed to detect pri-miR-15a, pri-miR-16-1, pri-miR-15b and pri-miR-21.

Primers and probe to detect miR-15a are:

```
Forward primer,
GTGTGTTTAAAAAAAATAAAACCTTGGA      (SEQ ID NO: 6)

Reverse primer,
TGGCCTGCACCTTTTCAAA               (SEQ ID NO: 7)

Probe,
AAAGTAGCAGCACATAATGGTTTGTGG       (SEQ ID NO: 8)
```

Primers and probe to detect miR-16-1 are:

```
Forward primer,
CAATATTTACGTGCTGCTAAGGCA          (SEQ ID NO: 78)

Reverse primer,
CAACCTTACTTCAGCAGCACAGTT          (SEQ ID NO: 79)

Probe,
CTGGAGATAATTTTAGAATCTTAACG        (SEQ ID NO: 80)
```

Primers and probe to detect miR-15b are:

```
Forward primer,
CAGTACTTTAAGGCCTCAAAAATGTAGG      (SEQ ID NO: 81)

Reverse primer,
CAAATAATGATTCGCATCTTGACTGT        (SEQ ID NO: 35)

Probe,
GCATGTAAACCATGATGTGCTGCT          (SEQ ID NO: 82)
```

Primers and probe to detect miR-21 are:

```
Forward primer,
ACCCGACAAGGTGGTACAGC              (SEQ ID NO: 83)

Reverse primer,
TCGACTGGTGTTGCCATGA               (SEQ ID NO: 53)

Probe,
ATTCAACAGTCAACATCAGTCTGATAAG      (SEQ ID NO: 84)
```

As indicated in the "Chemistry" column in Tables 8, "5-10-5" compounds are chimeric oligomeric compounds, composed of a gap segment 10 nucleotides in length which is comprised of 2'-deoxynucleotides. The "wing" segments on either side (5' and 3') of the oligomeric compound are comprised of five 2'-O-(2-methoxyethyl), also known as 2'-MOE, nucleotides. "5-10-7" compounds are chimeric oligomeric compounds, composed of a gap segment 10 nucleotides in length which is comprised of 2'-deoxynucleotides. The 5' wing segments is comprised of five 2'-MOE nucleotides and the 3' wing segment is comprised of seven 2'-MOE nucleotides. "Full 2'-MOE" oligomeric compounds are comprised of 2'-MOE nucleotides throughout. In all compounds in Tables 1 and 2, internucleoside (backbone) linkages are phosphorothioate (P=S) throughout, and all cytidine residues are 5-methylcytidines. In Table 8, "Drosha" indicates a Drosha recognition region; "MM" indicates a oligonucleotide having mismatches to a target sequence; "NC" indicates negative control; "Extended" is used to describe oligomeric compounds that are outside Drosha recognition regions; "Target" indicates the particular mature miRNA targeted by the oligomeric compound; and "Position on pri-miR-15a" indicates the site to which the oligomeric compounds are targeted on the pri-miR-15 a sequence (the compliment of nucleotides 31603159 to 31603468 of GENBANK® Accession number NT_024524.13, deposited with GENBANK® on Oct. 7, 2003).

Shown in Table 9 are levels observed for each target were normalized to 5.8S rRNA, and values were expressed relative to the untreated control (UTC). Each treatment was performed in duplicate.

TABLE 8

Oligomeric compounds targeted to pri-miR-15a

| Isis # | SEQUENCE | Motif | SEQ ID NO: | Target | Target Region | Position on pri-miR-15a |
|---|---|---|---|---|---|---|
| 345391 | TGTAAACCATGATGTGCTGCTA | 5-10-7 | 29 | miR-15b | None | None |
| 347964 | TATAACATTGATGTAATATG | 5-10-5 | 9 | miR-15a | Gapmer of 356213 NC, Extended | 12 |
| 347966 | TGCTACTTTACTCCAAGGTT | 5-10-5 | 11 | miR-15a | Gapmer of 356215 Drosha | 129 |
| 345411 | CACAAACCATTATGTGCTGCTA | 5-10-7 | 30 | miR-15a | Mature miR | 144 |
| 347980 | AGATCAGATCCTTGTATTTT | 5-10-5 | 25 | miR-15a | Gapmer of 356229 Drosha | 203 |
| 327901 | TGAGCTACAGTGCTTCATCTCA | Full 2'-MOE | 38 | miR-143 | None | None |
| 356213 | TATAACATTGATGTAATATG | Full 2'-MOE | 9 | miR-15a | NC, Extended | 12 |
| 360644 | GAATGCATGTAAAAAAATCT | Full 2'-MOE | 85 | miR-15a | Extended | 44 |
| 360643 | TCTTTCAGGAAAAAAAGAAT | Full 2'-MOE | 86 | miR-15a | Extended | 60 |
| 360642 | AATATAAAAATATTTTCTT | Full 2'-MOE | 87 | miR-15a | Extended | 76 |
| 360641 | ACATTCGCGCCTAAAGAATA | Full 2'-MOE | 88 | miR-15a | Extended | 92 |
| 360640 | TATTTTTTTAAACACACAT | Full 2'-MOE | 89 | miR-15a | Extended | 108 |
| 360639 | CTTTACTCCAAGGTTTTATT | Full 2'-MOE | 90 | miR-15a | Extended | 124 |
| 356215 | TGCTACTTTACTCCAAGGTT | Full 2'-MOE | 11 | miR-15a | Drosha | 129 |
| 327951 | CACAAACCATTATGTGCTGCTA | Full 2'-MOE | 30 | miR-15a | Mature miR | 144 |
| 356225 | TATTTTTGAGGCAGCACAAT | Full 2'-MOE | 21 | miR-15a | Drosha | 189 |
| 356228 | AGATCCTTGTATTTTTGAGG | Full 2'-MOE | 24 | miR-15a | Drosha | 198 |
| 356229 | AGATCAGATCCTTGTATTTT | Full 2'-MOE | 25 | miR-15a | Drosha | 203 |
| 356230 | AGAAGATCAGATCCTTGTAT | Full 2'-MOE | 26 | miR-15a | Drosha | 206 |
| 356231 | TTCAGAAGATCAGATCCTTG | Full 2'-MOE | 27 | miR-15a | Drosha | 209 |
| 356232 | AAATATATTTCTTCAGAAG | Full 2'-MOE | 28 | miR-15a | Drosha | 221 |
| 360647 | TAAGAGCTATGAATAAAAAG | Full 2'-MOE | 91 | miR-15a | Extended | 241 |
| 360648 | GCTGACATTGCTATCATAAG | Full 2'-MOE | 92 | miR-15a | Extended | 257 |
| 371778 | CTAAGGCACTGCTGACATTG | Full 2'-MOE | 93 | miR-16-1 | Drosha | 267 |

TABLE 8-continued

Oligomeric compounds targeted to pri-miR-15a

| Isis # | SEQUENCE | Motif | SEQ ID NO: | Target | Target Region | Position on pri-miR-15a |
|---|---|---|---|---|---|---|
| 360649 | GTGCTGCTAAGGCACTGCTG | Full 2'-MOE | 94 | miR-15a | Extended | 273 |
| 360650 | TAACGCCAATATTTACGTGC | Full 2'-MOE | 95 | miR-15a | Extended | 289 |
| 371783 | GTAGAGTATGGTCAACCTTACT | Full 2'-MOE | 96 | miR-16-1 | Drosha | 348 |
| 340927 | TGAGCTACAGTGCTTCATCTCA | 5-10-7 | 38 | miR-143 | None | None |
| 327927 | TGTAAACCATGATGTGCTGCTA | Full 2'-MOE | 29 | miR-15b | None | None |
| 342682 | CCTTCCCTGAAGGTTCCTCCT | Full 2'-MOE | 97 | MM | None | None |

TABLE 9

Pri-miR-15a, -15b, -16-1, and -21 levels following treatment of HeLa cells with oligomeric compounds targeted to pri-miR-15a

| ISIS # | SEQ ID NO: | Target | Target Region | Position on pri-miR-15a | pri-mir-15a | pri-miR-21 | pri-miR-15b | pri-miR-16-1 |
|---|---|---|---|---|---|---|---|---|
| 345391 | 29 | miR-15b | None | None | 0.61 | 0.9 | 0.4 | 1.6 |
| 347964 | 9 | miR-15a | Gapmer of 356213 NC, Extended | 12 | 0.27 | 1.2 | 0.5 | 0.5 |
| 347966 | 11 | miR-15a | Gapmer of 356215 Drosha | 129 | 0.14 | 1.7 | 0.4 | 0.4 |
| 345411 | 30 | miR-15a | Mature miR | 144 | 0.38 | 0.9 | 0.8 | 2.8 |
| 347980 | | miR-15a | Gapmer of 356229 Drosha | 203 | 0.93 | 0.9 | 0.5 | 0.7 |
| 327901 | 38 | miR-143 | None | None | 0.67 | 1.0 | 1.0 | 1.2 |
| 356213 | 9 | miR-15-a | NC, Extended | 12 | 0.83 | 1.7 | 0.5 | 0.4 |
| 360644 | 85 | miR-15-a | Extended | 44 | 0.60 | 1.5 | 0.9 | 0.2 |
| 360643 | 86 | miR-15-a | Extended | 60 | 0.65 | 1.4 | 0.8 | 0.9 |
| 360642 | 87 | miR-15-a | Extended | 76 | 0.51 | 1.4 | 0.5 | 0.8 |
| 360641 | 88 | miR-15-a | Extended | 92 | 1.25 | 1.9 | 2.2 | 1.2 |
| 360640 | 89 | miR-15-a | Extended | 108 | 0.99 | 1.4 | 0.9 | 0.6 |
| 360639 | 90 | miR-15-a | Extended | 124 | 2.68 | 1.0 | 0.8 | 0.8 |
| 356215 | 11 | miR-15a | Drosha | 129 | 3.45 | 1.3 | 1.1 | 0.9 |
| 327951 | 30 | miR-15a | Mature miR | 144 | 3.70 | 1.3 | 3.3 | 8.3 |
| 356225 | 21 | miR-15a | Drosha | 189 | 0.61 | 1.6 | 0.6 | 0.7 |
| 356228 | 24 | miR-15a | Drosha | 198 | 2.44 | 1.2 | 0.6 | 0.7 |
| 356229 | 25 | miR-15a | Drosha | 203 | 2.08 | 2.1 | 0.6 | 0.4 |
| 356230 | 26 | miR-15a | Drosha | 206 | 2.40 | 0.9 | 0.8 | 0.9 |
| 356231 | 27 | miR-15a | Drosha | 209 | 2.40 | 1.3 | 0.9 | 1.0 |
| 356232 | 28 | miR-15a | Drosha | 221 | 2.05 | 1.7 | 0.5 | 0.8 |
| 360647 | 91 | miR-15a | Extended | 241 | 0.62 | 1.7 | 0.8 | 1.1 |
| 360648 | 92 | miR-15a | Extended | 257 | 1.84 | 0.9 | 0.3 | 15.1 |
| 371778 | 93 | miR-16-1 | Drosha | 267 | 2.49 | 0.8 | 0.6 | 15.0 |
| 360649 | 94 | miR-15a | Extended | 273 | 3.00 | 1.6 | 1.0 | 23.9 |
| 360650 | 95 | miR-15a | Extended | 289 | 3.45 | 0.9 | 1.1 | 15.2 |
| 371783 | 96 | miR-16-1 | Drosha | 348 | 0.81 | 1.2 | 0.3 | 1.3 |
| 340927 | 38 | miR-143 | None | None | 0.62 | 1.0 | 0.7 | 0.7 |
| 327927 | 29 | miR-15b | None | None | 2.12 | 0.9 | 1.9 | 5.9 |
| 342682 | 97 | None | None | None | 0.85 | 1.5 | 1.1 | 1.0 |

Oligomeric compounds targeting mature miR-15a and mature miR-16 resulted in the highest increases in pri-miR-15 and pri-miR-16 levels RNA levels. The regions up to 16 nucleotides in the 5' direction relative to the 5' end of either the mature miR-15a sequence or the mature miR-16 sequence, and up to 40 nucleotides in the 3' direction relative to the 3' end of mature miR-15a, also resulted in increased pri-miRNA levels. An increase in pri-miR-15 a levels was seen with oligomeric compounds targeting the hairpin region of pri-miRNA, however, oligomeric compounds targeting the stem of the hairpin were more effective at increasing pri-miRNA levels as compared to oligomeric compounds targeting the loop region. Oligomeric compounds targeting mature miR-15a caused an increase in the levels of related pri-miR- 15a, pri-miR-15b and pri-miR-16. Oligomeric compounds targeting Drosha recognition regions did not cause the levels of a non-related pri-miRNA, pri-miR-21, to increase.

Oligomeric compounds targeting Drosha recognition regions affected pri-miR-15a and pri-miR-16-1 levels in different manners. For example, oligomeric compounds targeting the Drosha recognition region of miR-15a did not affect pri-miR-16-1 levels. Conversely, oligomeric compounds targeting Drosha recognition regions on pri-miR-16-1 increased pri-miR-16-1 and pri-miR-15a levels. It is known that miR-16 is preferentially processed relative to miR-15a, thus these data suggest that targeting the Drosha recognition region of a preferentially processed mature miRNA is a means by which a single oligomeric compound can be used to modulate the levels of multiple, related miRNAs.

Example 3

Effects of Oligomeric Compounds Targeting Pri-miRNAs and Mature miRs In Vivo

In a further embodiment, oligomeric compounds were tested in vivo to evaluate the effects of compounds targeting mature miRNAs, as well as the effects of oligomeric compounds which target Drosha cleavage sites. The miRNAs and pri-miRNAs selected were those corresponding to miR-15a and miR-21. The oligomeric compounds targeting the miR-15a mature miRNA. The oligomeric compounds targeting the mature miR-21 and Drosha cleavage site are ISIS 327917 and ISIS 358779 (GGTCAGATGAAAGATACCAA, SEQ ID NO: 69), respectively. These 4 compounds are uniformly comprised of 2'-MOE nucleotides and have phosphorothioate (P=S) internucleoside linkages throughout. All cytidine residues are 5-methylcytidines Male Balb/c mice, obtained from The Jackson Laboratories (Ben Harbor, Me.), were fed a standard rodent diet and were injected with 25 mg/kg of ISIS 327917, ISIS 358779, ISIS 327951 or ISIS 356415. Each treatment group contained a total of 5 animals. A control group received saline injections only. Injections were administered intraperitoneally, twice weekly for a period of 4 weeks. Animals were sacrificed after the final dose, and RNA was prepared from liver tissue. miR levels were measured by Northern blotting and normalized to U6 RNA, as described herein. The data are shown in Table 9 as the average of each treatment group.

TABLE 9

In vivo testing of oligomeric compounds targeting mature miRs and Drosha cleavage sites

|  | miR levels normalized to U6 RNA | |
| --- | --- | --- |
|  | miR-21 | miR-15a |
| Saline | 0.46 | 17.7 |
| ISIS 327917 (mature miR-21) | 0.33 | 19.5 |
| ISIS 358779 (miR-21, Drosha cleavage site) | 0.38 | 15.1 |
| ISIS 327951 (mature miR-15a) | 0.84 | 9.4 |
| ISIS 356215 (miR-15a, Drosha cleavage site) | 0.66 | 8.7 |

These data demonstrate that with regard to miR-21 and miR-15a, oligomeric compounds targeting Drosha cleavage sites and oligomeric compounds targeting mature miRNAs reduce miRNA expression to similar levels in vivo.

What is claimed:

1. A method of increasing the amounts of pri-miR-15 and pri-miR-16 in a cell comprising:
   contacting the cell with an oligomeric compound comprising an oligonucleotide consisting of 15 to 30 linked nucleosides and having a nucleobase sequence at least 90% complementary to a target region within nucleobases 257 to 308 of SEQ ID NO: 102, whereby the amounts of pri-miR-15 and pri-miR-16 in the cell are increased.

2. The method of claim 1 wherein the nucleobase sequence of the oligonucleotide is at least 95% complementary to a target region within nucleotides 257 to 308 of SEQ ID NO: 102.

3. The method of claim 1 wherein the nucleobase sequence of the oligonucleotide is 100% complementary to a target region within nucleobases 257 to 308 of SEQ ID NO 102.

4. The method of claim 1 wherein the oligonucleotide consists of 17 to 25 linked nucleosides.

5. The method of claim 1 wherein the oligomeric compound consists of an oligonucleotide.

6. The method of claim 1 wherein at least one nucleoside of the oligonucleotide comprises a sugar modification.

7. The method of claim 6 wherein each nucleoside of the oligonucleotide comprises a sugar modification.

8. The method of claim 7 wherein the sugar modification is 2'-O-methoxyethyl.

9. The method of claim 1 wherein at least one internucleoside linkage is a modified internucleoside linkage.

10. The method of claim 1 wherein each internucleoside linkage is a modified internucleoside linkage.

11. The method of claim 10 wherein the modified internucleoside linkage is a phosphorothioate internucleoside linkage.

12. The method of claim 1 wherein the oligonucleotide comprises at least one cytosine, wherein the cytosine is a 5-methylcytosine.

13. The method of claim 12 wherein each cytosine is a 5-methylcytosine.

14. The method of claim 1 wherein the oligonucleotide has a nucleobase sequence selected from the group consisting of SEQ ID NOs 92, 93, 94, and 95.

15. A method of increasing the amounts of pri-miR-15 and pri-miR-16 in a cell comprising:
   contacting the cell with an oligonucleotide consisting of 17 to 25 linked nucleosides and having a nucleobase sequence at least 90% complementary to a target region within nucleobases 257 to 308 of SEQ ID NO: 102, whereby the amounts of pri-miR-15 and pri-miR-16 in the cell are increased.

16. The method of claim 15 wherein each nucleoside comprises a sugar modification.

17. The method of claim 15 wherein each nucleoside comprises a 2'-O-methoxyethyl sugar modification.

18. The method of claim 17 wherein each internucleoside linkage is a phosphorothioate internucleoside linkage.

19. The method of claim 18 wherein the oligonucleotide comprises at least one cytosine and the cytosine is a 5-methylcytosine.

20. The method of claim 19 wherein the oligonucleotide has a nucleobase sequence selected from the group consisting of SEQ ID NOs 92, 93, 94, and 95.

* * * * *

SEQUENCE LISTING

```
<160> NUMBER OF SEQ ID NOS: 102

<210> SEQ ID NO 1
<211> LENGTH: 19
<212> TYPE: DNA
<213> ORGANISM: Artificial Sequence
<220> FEATURE:
<223> OTHER INFORMATION: Synthetic oligomeric compound

<400> SEQUENCE: 1
cgagaggcgg acgggaccg                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligomeric compound

<400> SEQUENCE: 2
gctctccgcc tgccctggc                                                    19

<210> SEQ ID NO 3
<211> LENGTH: 21
<212> TYPE: DNA
<213> ORGANISM: Artificial Sequence
<220> FEATURE:
<223> OTHER INFORMATION: Synthetic oligomeric compound
<220> FEATURE:
<221> NAME/KEY: misc_feature
```

```
<222> LOCATION: (1)...(19)
<223> OTHER INFORMATION: bases at these positions are RNA

<400> SEQUENCE: 3
cgagaggcgg acgggaccgt t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligomeric compound
<220> FEATURE:
<221> NAME/KEY: misc_feature
<222> LOCATION: (3)...(21)
<223> OTHER INFORMATION: bases at these positions are RNA

<400> SEQUENCE: 4
ttgcucuccg ccugcccugg c                                              21

<210> SEQ ID NO 5

<400> SEQUENCE: 5

000

<210> SEQ ID NO 6
<211> LENGTH: 28
<212> TYPE: DNA
<213> ORGANISM: Artificial Sequence
<220> FEATURE:
<223> OTHER INFORMATION: PCR Primer

<400> SEQUENCE: 6
gtgtgtttaa aaaaaataaa accttgga                                       28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
tggcctgcac cttttcaaa                                                 19

<210> SEQ ID NO 8
<211> LENGTH: 27
<212> TYPE: DNA
<213> ORGANISM: Artificial Sequence
<220> FEATURE:
<223> OTHER INFORMATION: PCR Probe

<400> SEQUENCE: 8
aaagtagcag cacataatgg tttgtgg                                        27

<210> SEQ ID NO 9
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 9
tataacattg atgtaatatg                                                20
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 10
gctactttac tccaaggttt                                             20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 11
tgctacttta ctccaaggtt                                             20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 12
gcaccttttc aaaatccaca                                             20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 13
cctgcacctt ttcaaaatcc                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 14
tggcctgcac cttttcaaaa                                             20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 15
atatggcctg caccttttca                                             20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligomeric compound
```

```
<400> SEQUENCE: 16
acaatatggc ctgcaccttt                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 17
agcacaatat ggcctgcacc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 18
ggcagcacaa tatggcctgc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 19
tgaggcagca caatatggcc                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 20
ttttgaggca gcacaatatg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 21
tatttttgag gcagcacaat                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 22
ttgtattttt gaggcagcac                                              20

<210> SEQ ID NO 23
<211> LENGTH: 20
```

<212> TYPE: DNA
<213> ORGANISM: Artificial Sequence
<220> FEATURE:
<223> OTHER INFORMATION: Synthetic oligomeric compound

<400> SEQUENCE: 23
tccttgtatt tttgaggcag                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 24
agatccttgt atttttgagg                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 25
agatcagatc cttgtatttt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 26
agaagatcag atccttgtat                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 27
ttcagaagat cagatccttg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 28
aaatatattt tcttcagaag                                              20

<210> SEQ ID NO 29
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 29
tgtaaaccat gatgtgctgc ta                                    22

<210> SEQ ID NO 30
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 30
cacaaaccat tatgtgctgc ta                                    22

<210> SEQ ID NO 31
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 31
cgttattaac ctccgttgaa                                       20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 32
atgcatacta cgaaaggccg                                       20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 33
ctgctagcct ctggatttga                                       20

<210> SEQ ID NO 34
<211> LENGTH: 28
<212> TYPE: DNA
<213> ORGANISM: Artificial Sequence
<220> FEATURE:
<223> OTHER INFORMATION: PCR Primer

<400> SEQUENCE: 34
cctacatttt tgaggcctta aagtactg                              28

<210> SEQ ID NO 35
<211> LENGTH: 26
<212> TYPE: DNA
<213> ORGANISM: Artificial Sequence
<220> FEATURE:
<223> OTHER INFORMATION: PCR Primer

<400> SEQUENCE: 35
caaataatga ttcgcatctt gactgt                                26

<210> SEQ ID NO 36
<211> LENGTH: 24
<212> TYPE: DNA
<213> ORGANISM: Artificial Sequence

```
<220> FEATURE:
<223> OTHER INFORMATION: PCR Probe

<400> SEQUENCE: 36
agcagcacat catggtttac atgc                                          24

<210> SEQ ID NO 37
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 37
ttagaatacg tcgcgttatg                                               20

<210> SEQ ID NO 38
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 38
tgagctacag tgcttcatct ca                                            22

<210> SEQ ID NO 39
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 39
ctgttcctgc tgaactgagc ca                                            22

<210> SEQ ID NO 40
<211> LENGTH: 15
<212> TYPE: DNA
<213> ORGANISM: Artificial Sequence
<220> FEATURE:
<223> OTHER INFORMATION: Synthetic oligomeric compound

<400> SEQUENCE: 40
ccctgggctc tgcct                                                    15

<210> SEQ ID NO 41
<211> LENGTH: 23
<212> TYPE: DNA
<213> ORGANISM: Artificial Sequence
<220> FEATURE:
<223> OTHER INFORMATION: PCR Primer

<400> SEQUENCE: 41
tgtacacaaa ccaactgtgt ttc                                           23

<210> SEQ ID NO 42
<211> LENGTH: 14
<212> TYPE: DNA
<213> ORGANISM: Artificial Sequence
<220> FEATURE:
<223> OTHER INFORMATION: PCR Primer

<400> SEQUENCE: 42
cgtgcctact gagc                                                     14
```

<210> SEQ ID NO 43
<211> LENGTH: 19
<212> TYPE: DNA
<213> ORGANISM: Artificial Sequence
<220> FEATURE:
<223> OTHER INFORMATION: PCR Probe

<400> SEQUENCE: 43
agcacaaact actacctca                                                  19

<210> SEQ ID NO 44
<211> LENGTH: 25
<212> TYPE: DNA
<213> ORGANISM: Artificial Sequence
<220> FEATURE:
<223> OTHER INFORMATION: PCR Primer

<400> SEQUENCE: 44
tgaggtagta gtttgtgctg ttggt                                           25

<210> SEQ ID NO 45
<211> LENGTH: 21
<212> TYPE: DNA
<213> ORGANISM: Artificial Sequence
<220> FEATURE:
<223> OTHER INFORMATION: PCR Primer

<400> SEQUENCE: 45
aggcagtagc ttgcgcagtt a                                               21

<210> SEQ ID NO 46
<211> LENGTH: 23
<212> TYPE: DNA
<213> ORGANISM: Artificial Sequence
<220> FEATURE:
<223> OTHER INFORMATION: PCR Probe

<400> SEQUENCE: 46
ttgtgacatt gcccgctgtg gag                                             23

<210> SEQ ID NO 47
<211> LENGTH: 21
<212> TYPE: DNA
<213> ORGANISM: Artificial Sequence
<220> FEATURE:
<223> OTHER INFORMATION: Synthetic oligomeric compound

<400> SEQUENCE: 47
actatgcaac ctactacctc t                                               21

<210> SEQ ID NO 48
<211> LENGTH: 24
<212> TYPE: DNA
<213> ORGANISM: Artificial Sequence
<220> FEATURE:
<223> OTHER INFORMATION: PCR Primer

<400> SEQUENCE: 48
cctaggaaga ggtagtaggt tgca                                            24

<210> SEQ ID NO 49
<211> LENGTH: 25
<212> TYPE: DNA
<213> ORGANISM: Artificial Sequence
<220> FEATURE:
<223> OTHER INFORMATION: PCR Primer

```
<400> SEQUENCE: 49
cagcaggtcg tatagttacc tcctt                                        25

<210> SEQ ID NO 50
<211> LENGTH: 25
<212> TYPE: DNA
<213> ORGANISM: Artificial Sequence
<220> FEATURE:
<223> OTHER INFORMATION: PCR Probe

<400> SEQUENCE: 50
agttttaggg cagggatttt gccca                                        25

<210> SEQ ID NO 51
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 51
tcaacatcag tctgataagc ta                                           22

<210> SEQ ID NO 52
<211> LENGTH: 20
<212> TYPE: DNA
<213> ORGANISM: Artificial Sequence
<220> FEATURE:
<223> OTHER INFORMATION: PCR Primer

<400> SEQUENCE: 52
gctgtaccac cttgtcgggt                                              20

<210> SEQ ID NO 53
<211> LENGTH: 19
<212> TYPE: DNA
<213> ORGANISM: Artificial Sequence
<220> FEATURE:
<223> OTHER INFORMATION: PCR Primer

<400> SEQUENCE: 53
tcgactggtg ttgccatga                                               19

<210> SEQ ID NO 54
<211> LENGTH: 28
<212> TYPE: DNA
<213> ORGANISM: Artificial Sequence
<220> FEATURE:
<223> OTHER INFORMATION: PCR Probe

<400> SEQUENCE: 54
cttatcagac tgatgttgac tgttgaat                                     28

<210> SEQ ID NO 55
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 55
acaagcagac agtcaggcag                                              20

<210> SEQ ID NO 56
```

```
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 56
ggtaggcaaa acaagcagac                                                  20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 57
ggagatgtca cgatggtagg                                                  20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 58
aggtggtaca gccatggaga                                                  20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 59
gataagctac ccgacaaggt                                                  20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 60
agtctgataa gctacccgac                                                  20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 61
caacagtcaa catcagtctg                                                  20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 62
```

```
gagattcaac agtcaacatc                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 63
ctggtgttgc catgagattc                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 64
catcgactgg tgttgccatg                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 65
acagcccatc gactggtgtt                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 66
tgtcagacag cccatcgact                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 67
ccaaaatgtc agacagccca                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 68
gataccaaaa tgtcagacag                                              20

<210> SEQ ID NO 69
<211> LENGTH: 20
<212> TYPE: DNA
```

```
<213> ORGANISM: Artificial Sequence
<220> FEATURE:
<223> OTHER INFORMATION: Synthetic oligomeric compound

<400> SEQUENCE: 69
ggtcagatga aagataccaa                                                    20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 70
aacattggat atggatggtc                                                    20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 71
taatgtttaa atgagaacat                                                    20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 72
aacaatgatg ctgggtaatg                                                    20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 73
gagtttctga ttataaacaa                                                    20

<210> SEQ ID NO 74
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 74
cgacaaggtg gtacagccat                                                    20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 75
gaaagatacc aaaatgtcag                                                    20
```

```
<210> SEQ ID NO 76
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 76
acgctagcct aatagcgagg                                              20

<210> SEQ ID NO 77
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 77
ccttccctga aggttcctcc tt                                           22

<210> SEQ ID NO 78
<211> LENGTH: 24
<212> TYPE: DNA
<213> ORGANISM: Artificial Sequence
<220> FEATURE:
<223> OTHER INFORMATION: PCR Primer

<400> SEQUENCE: 78
caatatttac gtgctgctaa ggca                                         24

<210> SEQ ID NO 79
<211> LENGTH: 24
<212> TYPE: DNA
<213> ORGANISM: Artificial Sequence
<220> FEATURE:
<223> OTHER INFORMATION: PCR Primer

<400> SEQUENCE: 79
caaccttact tcagcagcac agtt                                         24

<210> SEQ ID NO 80
<211> LENGTH: 26
<212> TYPE: DNA
<213> ORGANISM: Artificial Sequence
<220> FEATURE:
<223> OTHER INFORMATION: PCR Probe

<400> SEQUENCE: 80
ctggagataa ttttagaatc ttaacg                                       26

<210> SEQ ID NO 81
<211> LENGTH: 28
<212> TYPE: DNA
<213> ORGANISM: Artificial Sequence
<220> FEATURE:
<223> OTHER INFORMATION: PCR Primer

<400> SEQUENCE: 81
cagtacttta aggcctcaaa aatgtagg                                     28

<210> SEQ ID NO 82
<211> LENGTH: 24
<212> TYPE: DNA
<213> ORGANISM: Artificial Sequence
<220> FEATURE:
```

<223> OTHER INFORMATION: PCR Probe

<400> SEQUENCE: 82
gcatgtaaac catgatgtgc tgct                                    24

<210> SEQ ID NO 83
<211> LENGTH: 20
<212> TYPE: DNA
<213> ORGANISM: Artificial Sequence
<220> FEATURE:
<223> OTHER INFORMATION: PCR Primer

<400> SEQUENCE: 83
acccgacaag gtggtacagc                                         20

<210> SEQ ID NO 84
<211> LENGTH: 28
<212> TYPE: DNA
<213> ORGANISM: Artificial Sequence
<220> FEATURE:
<223> OTHER INFORMATION: PCR Probe

<400> SEQUENCE: 84
attcaacagt caacatcagt ctgataag                                28

<210> SEQ ID NO 85
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 85
gaatgcatgt aaaaaaatct                                         20

<210> SEQ ID NO 86
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 86
tctttcagga aaaaagaat                                          20

<210> SEQ ID NO 87
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 87
aatataaaaa atattttctt                                         20

<210> SEQ ID NO 88
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 88
acattcgcgc ctaaagaata                                         20

```
<210> SEQ ID NO 89
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 89 tattttttt aaacacacat                                            20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 90
ctttactcca aggttttatt                                           20

<210> SEQ ID NO 91
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 91
taagagctat gaataaaaag                                           20

<210> SEQ ID NO 92
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 92
gctgacattg ctatcataag                                           20

<210> SEQ ID NO 93
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 93
ctaaggcact gctgacattg                                           20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligomeric compound

<400> SEQUENCE: 94
gtgctgctaa ggcactgctg                                           20

<210> SEQ ID NO 95
<211> LENGTH: 20
<212> TYPE: DNA
<213> ORGANISM: Artificial Sequence
<220> FEATURE:
<223> OTHER INFORMATION: Synthetic oligomeric compound
```

<400> SEQUENCE: 95
taacgccaat atttacgtgc								20

<210> SEQ ID NO 96
<211> LENGTH: 22
<212> TYPE: DNA
<213> ORGANISM: Artificial Sequence
<220> FEATURE:
<223> OTHER INFORMATION: Synthetic oligomeric compound

<400> SEQUENCE: 96
gtagagtatg gtcaaccttta ct							22

<210> SEQ ID NO 97
<211> LENGTH: 21
<212> TYPE: DNA
<213> ORGANISM: Artificial Sequence
<220> FEATURE:
<223> OTHER INFORMATION: Synthetic oligomeric compound

<400> SEQUENCE: 97
ccttccctga aggttcctcc t							21

<210> SEQ ID NO 98
<211> LENGTH: 22
<212> TYPE: RNA
<213> ORGANISM: Artificial Sequence
<220> FEATURE:
<223> OTHER INFORMATION: Synthetic oligomeric compound

<400> SEQUENCE: 98
uagcagcaca uaaugguuug ug							22

<210> SEQ ID NO 99
<211> LENGTH: 22
<212> TYPE: RNA
<213> ORGANISM: Artificial Sequence
<220> FEATURE:
<223> OTHER INFORMATION: Synthetic oligomeric compound

<400> SEQUENCE: 99
uagcagcaca ucaugguuua ca							22

<210> SEQ ID NO 100
<211> LENGTH: 22
<212> TYPE: RNA
<213> ORGANISM: Artificial Sequence
<220> FEATURE:
<223> OTHER INFORMATION: Synthetic oligomeric compound

<400> SEQUENCE: 100
uagcagcacg uaaauauugg cg							22

<210> SEQ ID NO 101
<211> LENGTH: 21
<212> TYPE: RNA
<213> ORGANISM: Artificial Sequence
<220> FEATURE:
<223> OTHER INFORMATION: Synthetic oligomeric compound

<400> SEQUENCE: 101
uagcagcaca gaaauauugg c							21

<210> SEQ ID NO 102
<211> LENGTH: 310

```
<212> TYPE: DNA
<213> ORGANISM: Homo sapien

<400> SEQUENCE: 102
aaataattat gcatattaca tcaatgttat aatgtttaaa catagatttt tttacatgca      60 ttctttttt  cctgaaagaa aatatttttt atattcttta ggcgcgaatg tgtgtttaaa     120
aaaaataaaa ccttggagta aagtagcagc acataatggt ttgtggattt tgaaaaggtg    180
caggccatat tgtgctgcct caaaaataca aggatctgat cttctgaaga aaatatattt    240 cttttattc  atagctctta tgatagcaat gtcagcagtg ccttagcagc acgtaaatat    300
tggcgttaag                                                             310
```